(12) United States Patent
Beaty

(10) Patent No.: US 9,395,332 B2
(45) Date of Patent: Jul. 19, 2016

(54) CONTROLLED SLEW RATE TRANSITION FOR ELECTROCHEMICAL ANALYSIS

(71) Applicant: Roche Diabetes Care, Inc., Indianapolis, IN (US)

(72) Inventor: Terry A Beaty, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 502 days.

(21) Appl. No.: 13/920,117

(22) Filed: Jun. 18, 2013

(65) Prior Publication Data

US 2013/0277235 A1 Oct. 24, 2013

Related U.S. Application Data

(63) Continuation of application No. PCT/EP2011/006342, filed on Dec. 14, 2011.

(60) Provisional application No. 61/424,856, filed on Dec. 20, 2010.

(51) Int. Cl.
*G01N 27/327* (2006.01)
*G01N 27/48* (2006.01)

(52) U.S. Cl.
CPC ............ *G01N 27/48* (2013.01); *G01N 27/3273* (2013.01)

(58) Field of Classification Search
CPC ..................................... G01N 27/327–27/3274
See application file for complete search history.

(56) References Cited

U.S. PATENT DOCUMENTS

| 5,108,564 | A | 4/1992 | Szuminsky et al. | |
| 7,545,148 | B2 | 6/2009 | Lorimer et al. | |
| 2010/0213079 | A1* | 8/2010 | Willis | A61B 5/14532 205/775 |

FOREIGN PATENT DOCUMENTS

| GB | 1448367 A | 9/1976 |
| WO | 03/056319 A3 | 7/2003 |

OTHER PUBLICATIONS

Operator's Manual for Gamry Instrument PCI4 Potentiostat/Galvanostat/ZRA, published Feb. 28, 2011.*
Bartak, D. E. et al., "A Function Generator for Electroanalytical Experiments," Chemical Instrumentation, 1972, pp. 1-13, vol. 4, No. 1.
Yuan, Xiang and Von Wandruszka, Ray, "Precapacitive Processes in Single Potential-Step Chronoamperometry," Talanta, 1991, pp. 189-194, vol. 38, No. 2.

* cited by examiner

*Primary Examiner* — Alexander Noguerola
(74) *Attorney, Agent, or Firm* — Roche Diabetes Care, Inc.

(57) ABSTRACT

Measurement systems and methods are disclosed for minimizing the effects created by a meter's output amplifier during electrochemical measurements. In the systems and methods, transition of an excitation potential applied between electrodes of a test strip is controlled so that it is at a sufficiently slow rate below a slew rate capability of the system (but still fast enough to minimally impact overall test time) to reduce variability in the test results. The methods and systems therefore use a transition having a ramp-shaped waveform, a sinusoidal-shaped waveform or an exponential-shaped waveform. Additionally, the excitation potential can be purposefully controlled by a processor, memory driven digital-to-analog converter or external circuitry at a rate sufficiently slow to make variations in the analog electronics slew rate insignificant for all sample types and test conditions.

19 Claims, 27 Drawing Sheets

CONTROLLED SLEW RATE TRANSITION FOR ELECTROCHEMICAL ANALYSIS

CROSS-REFERENCE TO RELATED APPLICATIONS

This patent application is a continuation of Int'l Patent Application No. PCT/EP2011/006342; filed 14 Dec. 2011, which claims the benefit of U.S. Provisional Patent Application No. 61/424,856; filed 20 Dec. 2010. Each patent application is incorporated herein by reference as if set forth in its entirety.

TECHNICAL FIELD

The invention relates generally to engineering and electrochemistry, and more particularly to systems and methods that minimize undesirable effects created by an electrochemical potentiostat's output amplifier during amperometric measurements.

BACKGROUND

Home monitoring of various biological conditions, such as diabetes, has become quite common in recent years. With the advent of home monitoring, there has been a need for the measurements to be accurate and precise. When controlling measurement precision, there are a number of possible sources for error, including the characteristics of the sample itself (e.g., hematocrit, temperature, etc.), the characteristics of the test strip (e.g., sample receiving cell, electrode dimensions, reagent properties, etc.) and the electrical characteristics of the potentiostat and measurement electronics. For instance, potential step chronoamperometry measurement errors can occur when attempting to apply an ideal potential difference step between working and counter/reference electrodes of a potentiostat connected to an electrochemical cell with a solution-conductor interface. This interface behaves as a capacitor and will pass current until it is charged. The initial capacitive charging current can be quite large in a very short time frame.

Conventional chronoamperometric electrochemical methods generally apply a constant potential or a potential step of sufficient amplitude to initiate the redox reaction of interest and to measure the resulting charge or current generated, which is proportional to the analyte concentration. See, e.g., U.S. Pat. Nos. 4,233,029; 4,225,410; 4,323,536; 4,008,448; 4,654,197; 5,108,564; 5,120,420; 5,128,015; 5,243,516; 5,437,999; 5,288,636; 5,628,890; 5,682,884; 5,727,548; 5,997,817; 6,004,441; 4,919,770; and 6,054,039.

When attempting to apply an ideal potential step, the actual potential difference profile and the resulting current may be undesirably influenced by the potentiostat and electrochemical cell characteristics. These include the working electrode area, the bulk resistivity of the sample, and the initial conductivity of an overlying reagent layer, as well as the potentiostat's output amplifier transient response. An operational amplifier's ability to drive a capacitive load is affected by its internal parameters such as output impedance, slew rate, gain-bandwidth product, and circuit design such as the attenuation phase margin and phase shift of the feedback circuit. A number of these factors are further affected by amplifier operating temperature, manufacturing process and power supply filtering. The amplifier's output impedance is one of the more significant factors affecting performance with capacitive loads.

With home monitoring systems, meters have been designed with expense in mind. A common meter potentiostat design incorporates an operational amplifier with a unity-gain voltage follower configuration. However, such a voltage follower configuration is highly susceptible to instability at short times after a potential step is applied, especially when driving a capacitive load through a small series resistance. These issues make it difficult and more expensive to develop new test strips and/or meters to consistently reproduce a potentiostat's electrical response across various solution-test strip electrode-meter-environmental combinations. For instance, even minor changes to the test strip and/or meter can dramatically change the deviation of an ideal potential step applied to the sample in a wetted test strip. Any potentiostat response that deviates from an ideal potential step or varies with a cell's capacitance or conductivity is an undesirable source of variability in a measurement system. This variability's effects are detectable in the amperometric response precision long after the potential transition has stabilized. As result, either an uncontrolled error source is introduced into electrochemical measurements or a significant amount of time and expense is devoted to refining the potentiostat circuit design to tolerate the sample conductivity and sensor architecture when any changes are made.

For the foregoing reasons, there is a need for improvement in this field.

BRIEF SUMMARY

The inventors have discovered that it is desirable to develop a measurement system with an inexpensive and easily reproducible potential stimulus circuit that provides a functional equivalent of an ideal potential step while at the same time minimizes sensitivity of the amplifier circuit's parameters, power reserve and/or the sample's uncompensated resistance as well as effective capacitance. It was found that the potential change at a working electrode in response to a step function is nominally an exponential rise. Ideally, the exponential rise time is governed by the sample's cell time constant, $R_U C_D$. This time constant defines the shortest time over which a cell will permit significant perturbation.

There is little value in attempting to impose any potential transition with a slew rate that is much less than the cell's time constant. $R_U$ is the uncompensated solution resistance, and may include uncompensated electrode lead resistance. $C_D$ is the double layer capacitance, which is directly proportional to the electrode area. These parameters may vary depending on the electrode architecture, sample properties and temperature. Expected values for $C_D$ range from about 10-50 µF/cm². Estimates for $C_D$ in commercially available biosensors are about 10-500 nF, depending on electrode composition and area, with typical values of about 50-100 nF. Total $R_U$ values may have a comparable range based on conductivity of the electrode leads, reagent formulation and sample type. Fluid sample (e.g., blood) conductivity varies, increasing with temperature, electrolytes concentration, reduced red blood cell volume or decreasing serum proteins. In the case of whole blood samples, typical physiological values range from about 3-10 mS/cm at room temperature, nominal hematocrit (HCT) with no salt variation. Uncompensated resistance values could be as low as about 20Ω for a fairly conductive (e.g., about 30 mS/cm) aqueous test solution to about 5,000Ω for a 70% hematocrit blood sample at low temperature.

More particularly, it was found that an operational amplifier's potential step response with a capacitive load may create excitation instability, resulting in undesirable variation in the amperometric response, which makes the measurement inherently less precise. In other words, limitations in slew rate capability of the meter system itself can give rise to undesirable effects in the amplifier. To address this issue, a potentiostat's "step" excitation transition is applied and controlled by a processor and/or memory driven analog-to-digital converter at a rate sufficiently slow to make changes in the analog electronic's slew rate generally insignificant regardless of sample, test strip, instrument electronics and environmental conditions. The potential transition is sufficiently fast to minimize the impact on the current response and the overall interrogation time. With this technique, test results are easily replicated, sample insensitive, and most significantly, produce more precise results at earlier times.

In one aspect, the transition of the excitation potential applied between the electrodes of the test strip is controlled so that it is at a rate sufficiently slower than the slew rate capability of the potentiostat and measurement electronics, regardless of capacitive load, but still fast enough to emulate a potential step and minimally impact overall test time, so as to minimize the potentiostat transient response requirements, reduce variability in the current response and improve test result reproducibility. In one embodiment, a 450 mV excitation potential is applied in which the transition time is greater than about 500 μsec (900 V/sec slew rate). As used herein, "slew rate" generally means the rate of potential transition or rate of potential excitation rise when referring to application of the potential between electrodes. At this rate, the slew rate is still acceptably rapid to present a minimal impact on the resulting current and overall sample interrogation time. Again, the excitation voltage transition can be purposefully controlled by a processor, memory driven digital-to-analog converter or potentiostat circuit design at a rate sufficiently slow to make changes in the analog electronics slew rate insignificant for all test conditions.

The transition excitation may be controlled by any time continuous controlled function, such as a linear ramp or exponential rise. As will be discussed below, programming a transition time to be greater than (or equal to) about 500 μsec provides an adequate time to reduce influences by the system's transient response. Because the potential at the working electrode transitions from 0 to 450 mV, the potentiostat electrodes are excited at a maximum transition rate of 900 V/sec. The systems therefore are inherently more reproducible with less variability because the potentiostat is not required to predictably respond to the transients required to support an ideal step function.

This disclosure addresses the issue of measurement errors created by electrochemically analyzing glucose concentrations in blood with the same type of test strips on at least two different meter platforms that have different slew rate capabilities. This issue is addressed by each of the different meter platforms executing an analysis protocol in which each meter platform applies to the electrodes of the test strips excitation potential differences with transition times of at least 5 msec.

These and other advantages, effects, features and objects of the invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
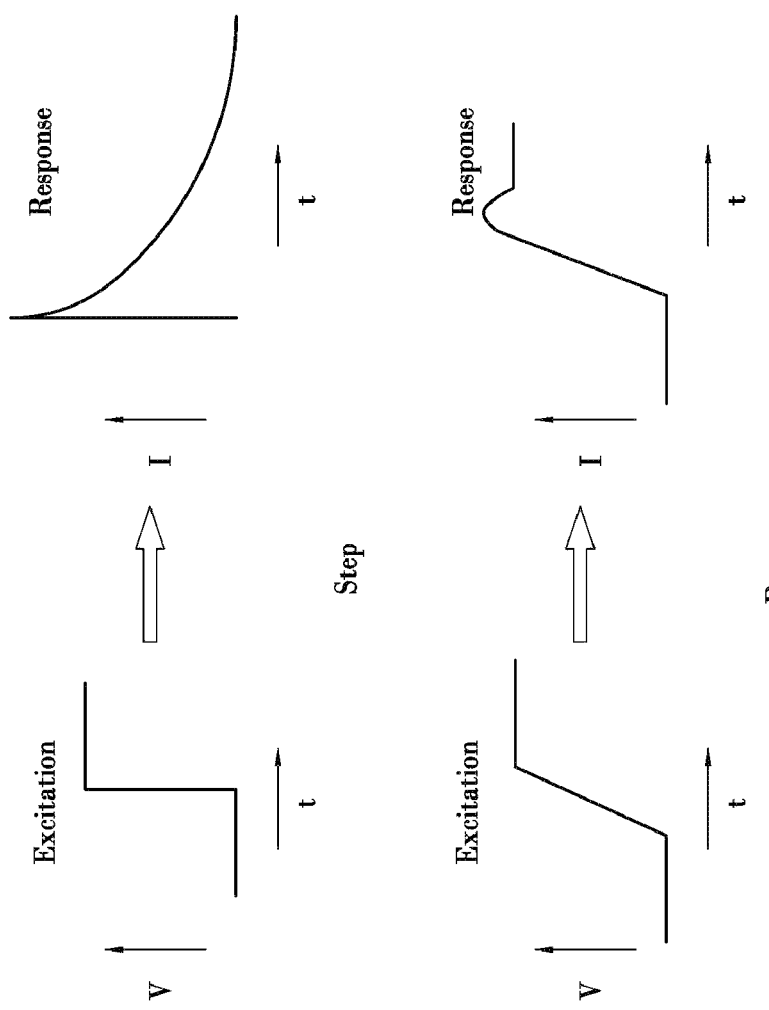
FIG. 1 is a diagram comparing current responses between a step-type excitation and a ramp-type excitation.

While the present invention is susceptible to various modifications and alternative forms, exemplary embodiments thereof are shown by way of example in the drawings and are herein described in detail. It should be understood, however, that the description of exemplary embodiments that follows is not intended to limit the invention to the particular forms disclosed, but on the contrary, the intention is to cover all advantages, effects, features and objects falling within the spirit and scope of the invention as defined by the embodiments above and the claims below. Reference should therefore be made to the embodiments above and claims below for interpreting the scope of the invention. As such, it should be noted that the embodiments described herein may have advantages, effects, features and objects useful in solving other problems.

DESCRIPTION OF PREFERRED EMBODIMENTS

The systems and methods now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements Likewise, many modifications and other embodiments of the systems and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

Overview

Figure 2:
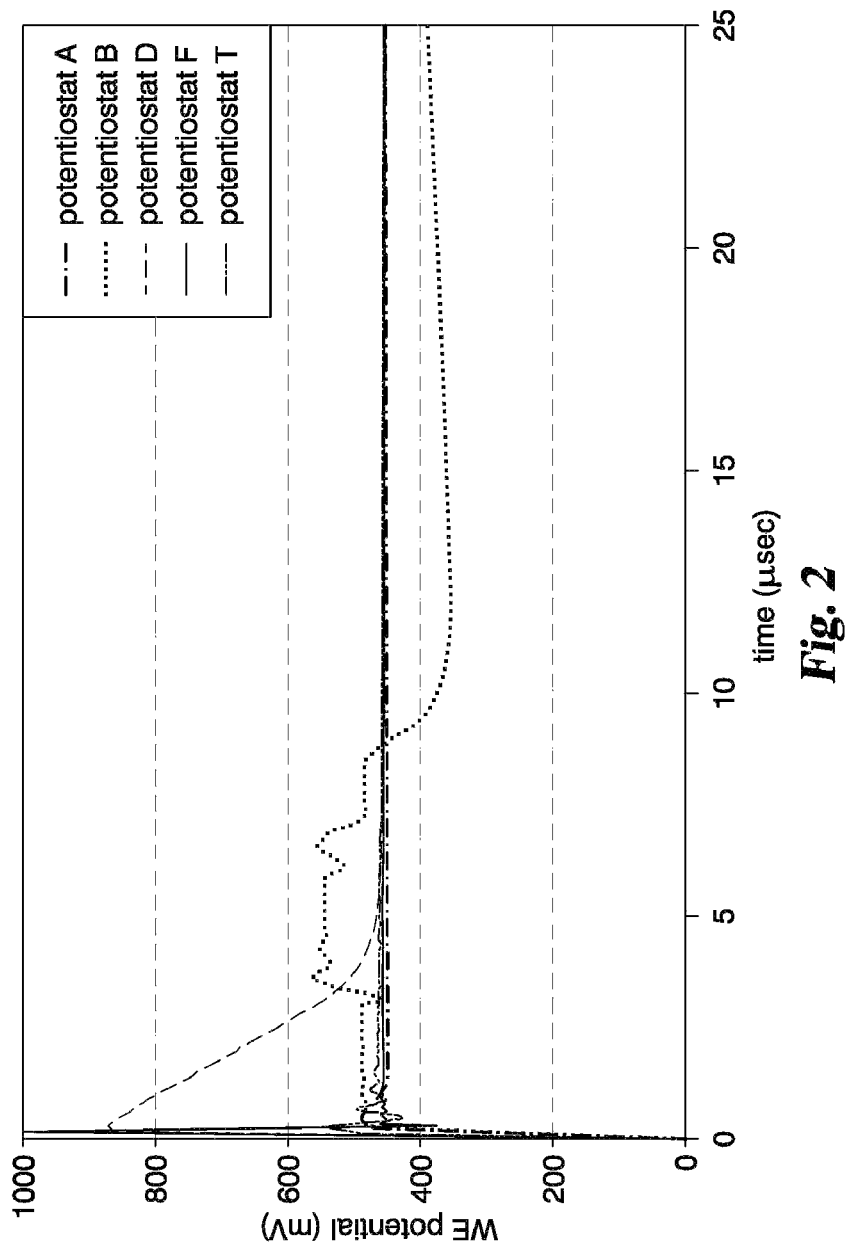
FIG. 2 is a graph comparing the potential transient response of different potentiostats attempting to apply a 450 mV potential step to the working electrode of a test strip containing an aqueous glucose test solution with conductivity about 1.5 mS/cm.
Figure 3:
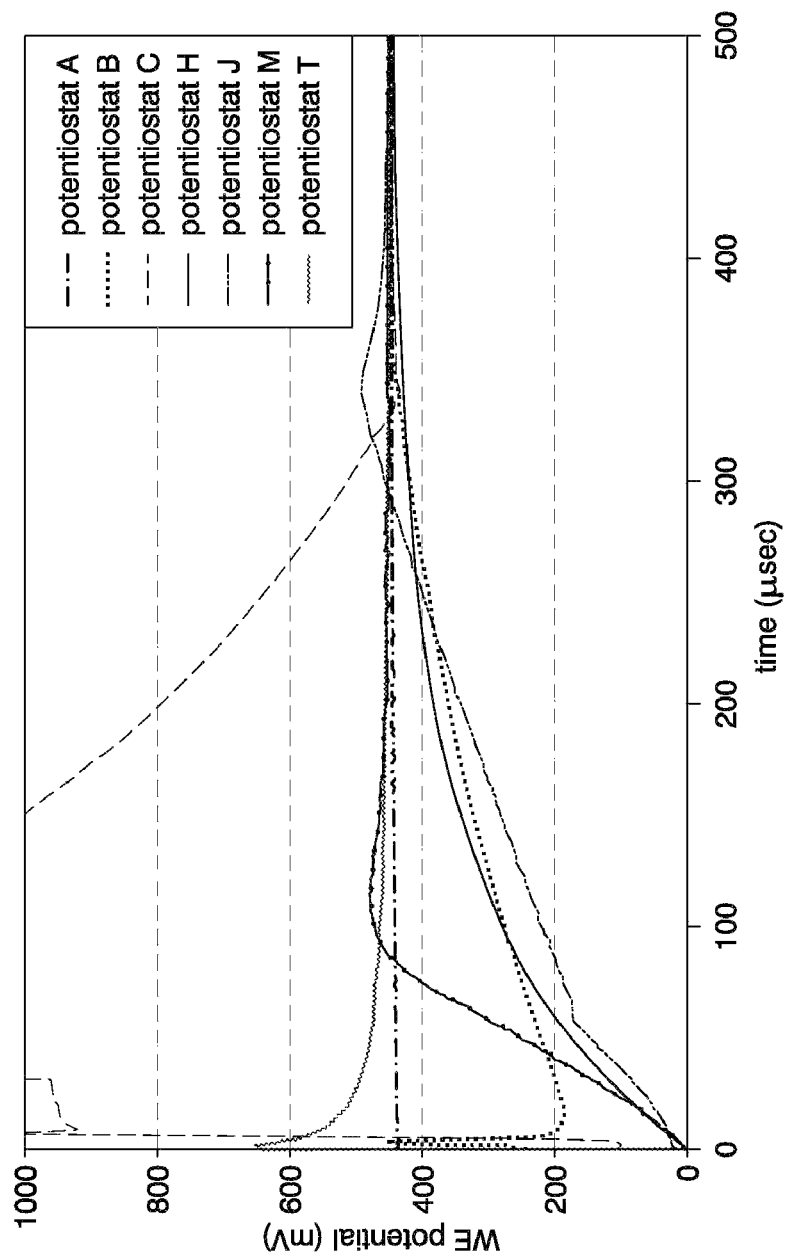
FIG. 3 is a graph comparing the potential transient response of different potentiostats attempting to apply a 450 mV potential step to the working electrode of a test strip containing an aqueous glucose test solution with conductivity about 30 mS/cm.

As mentioned above, it was discovered that by controlling the transition of the step potential applied between the electrodes of the test strip at a rate sufficiently slower than the slew rate capability of the potentiostat and longer than the electrochemical cell's time constant (but still fast enough to minimally impact overall test time), the variability of the test results is reduced, and the reproducibility of the results improved. FIG. 1 generally illustrates this concept. As can be seen at the top of FIG. 1, when a potential step excitation is applied to the working electrode of a test strip containing a sample, the resulting current response has a pronounced peak current typically associated with capacitive charging. In an ideal potentiostat, the charging current can be quite large as time approaches zero. In practice, no potentiostat can produce an ideal excitation step with no time dependent potential transition into a capacitive load, or source/sink an unlimited amount of current, even for very short periods. As a result, the actual excitation transition will be influenced by the transient response of the potentiostat, which is in turn influenced by the electrode and sample properties. In contrast, when the potential is gradually applied over time at a rate significantly slower than the potentiostat's slew rate and longer than electrochemical cell's time constant, such as by a ramped excitation, rather than attempting a potential step, the resulting current has a lower peak value. This reduction in the peak current in turn facilitates a less demanding potentiostat design. The excitation's transient response is more predictable, which provides more consistent excitation transitions across a wide range of sample conductivity and meter platforms. Consequently, the current response precision is improved. The time and expense devoted to refining the fundamental circuit design of the meter in order to match the sensor architecture when changes are made can be dramatically reduced. By adopting such a potential transitioning technique, a number of error sources, such as those caused by the characteristics of the sample itself, the characteristics of the test strip, and the characteristics of the meter, can be reduced. FIG. 2 shows that when attempting to apply a potential step to moderately resistive electrochemical loads (e.g., around 1.5 mS/cm test solution) using different potentiostats, the resulting potential transient can vary slightly between circuit implementations. In a somewhat similar fashion, FIG. 3 shows pronounced variations in the resulting potential transient when different potentiostats attempt to apply a potential step to moderately conductive electrochemical loads (e.g., around 30 mS/cm test solution). When attempting to impose a potential step to a more conductive cell, a potentiostat's transient response is much less predictable in both amplitude and duration.

Figure 4:
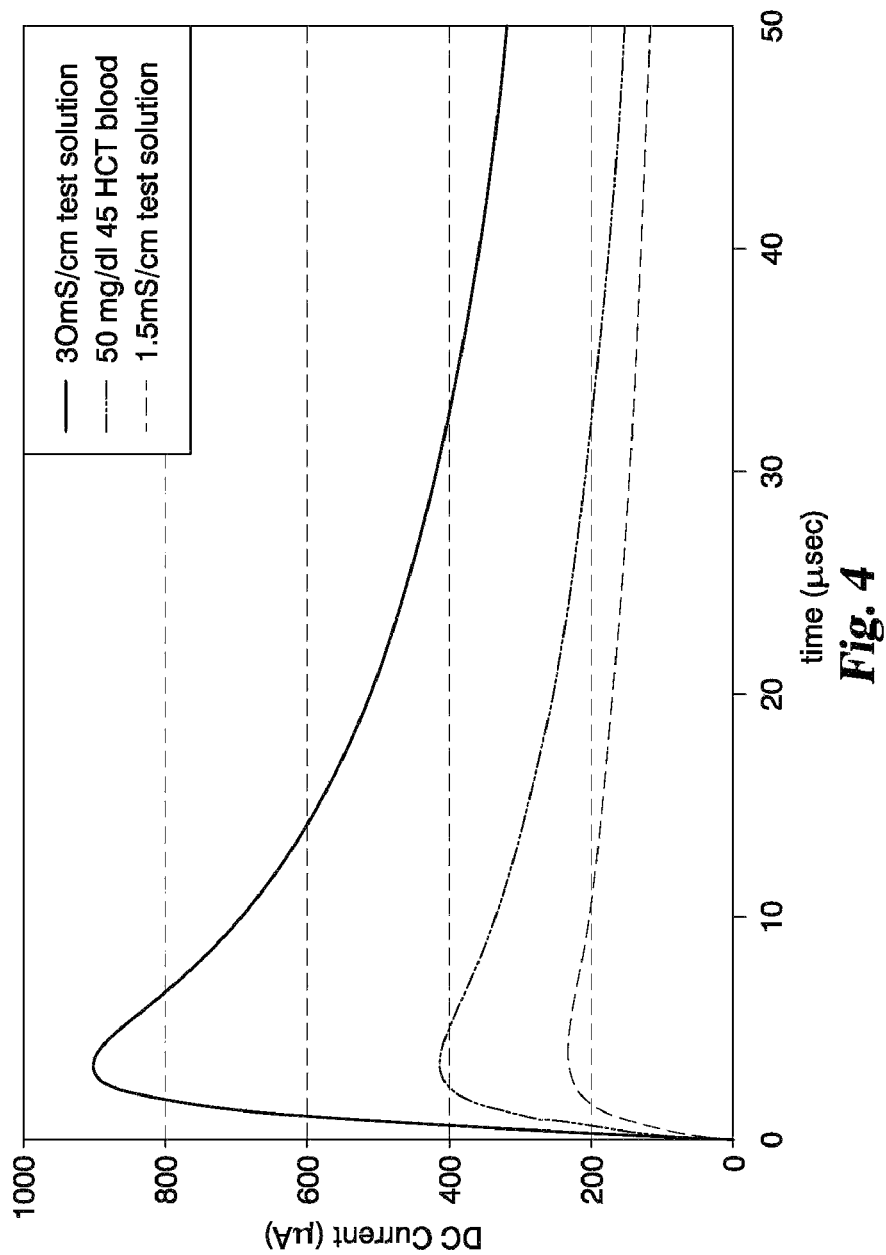
FIG. 4 is a graph comparing a stepped potential's peak current from a high bandwidth, low slew rate potentiostat for one type of biosensor wetted with different conductivity test solutions and comparable glucose concentrations.
Figure 5:
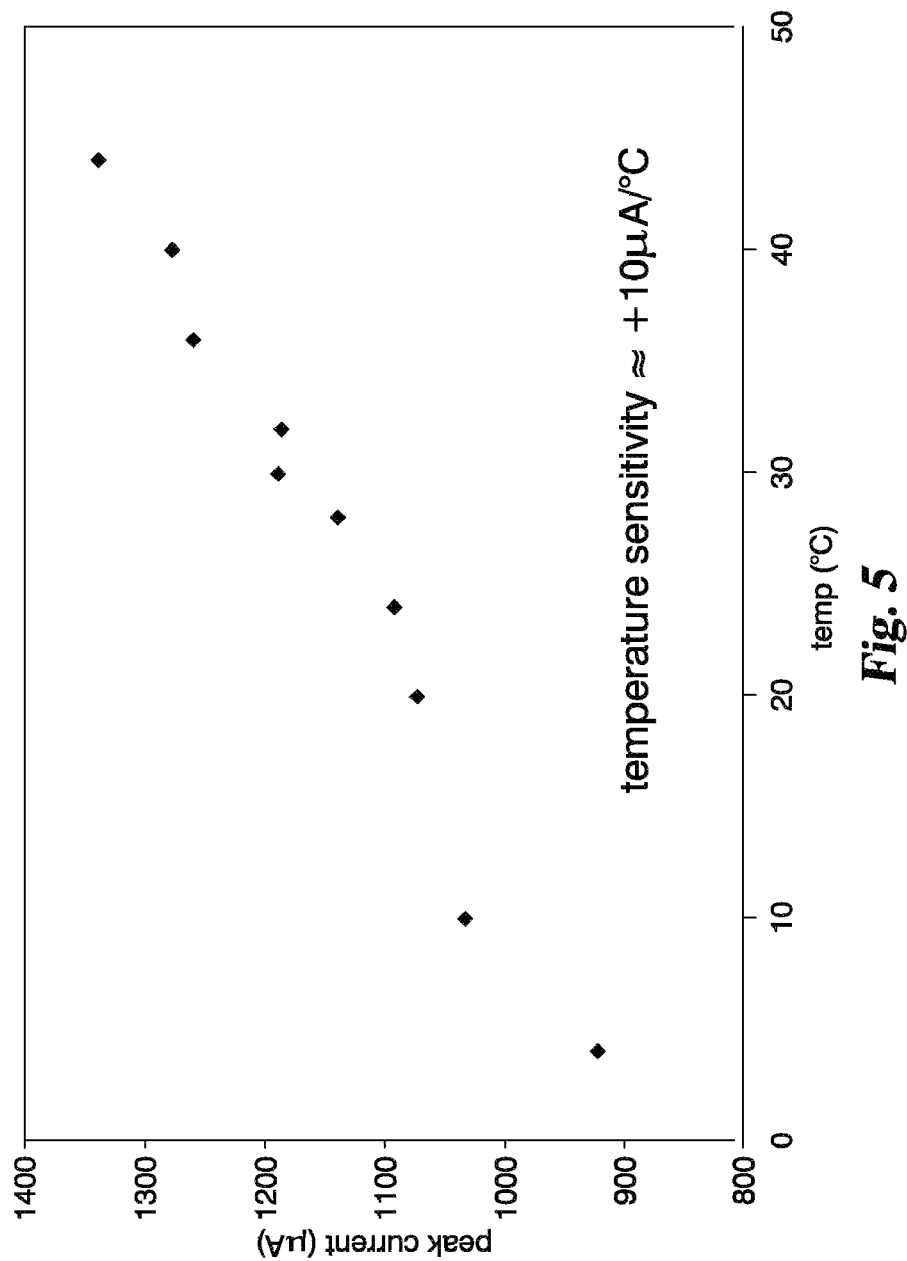
FIG. 5 is a graph of a typical biosensor's peak current temperature sensitivity in response to a potential step using a high bandwidth potentiostat using a 30 mS/cm aqueous test solution.

FIGS. 4 and 5 highlight one of the sources of difficulties with this transient response. FIG. 4 shows the peak current generated by applying a 450 mV potential step with an exceptionally fast potentiostat to identical biosensors wetted with test solutions with varying conductivity. For example, depending on the solution conductivity and electrode geometry, the peak current in response to a nearly ideal potential step excitation can produce currents of about 1000 nA in less than about 5 μsec for a 30 mS/cm test solution and 0.35 mm$^2$ electrode. Given the equation for a current through a capacitor I=C(dV/dt), the slew rate necessary to support 1000 μA into a 50 nF cell capacitance should be greater than 2000 V/sec.

Additionally, every amplifier has some settling time associated with a step transition. Values up to about 10 μsec are common for inexpensive, commercially available devices driving a load of about 100 pF. This settling time extends beyond the time necessary to reach peak current, and settling time will increase as load capacitance increases above 100 pF. FIG. 5 shows that the 30 mS/cm test solution's peak current response generally increases as the temperature increases. The systems and methods described herein address these as well as other sources of error.

Figure 6:
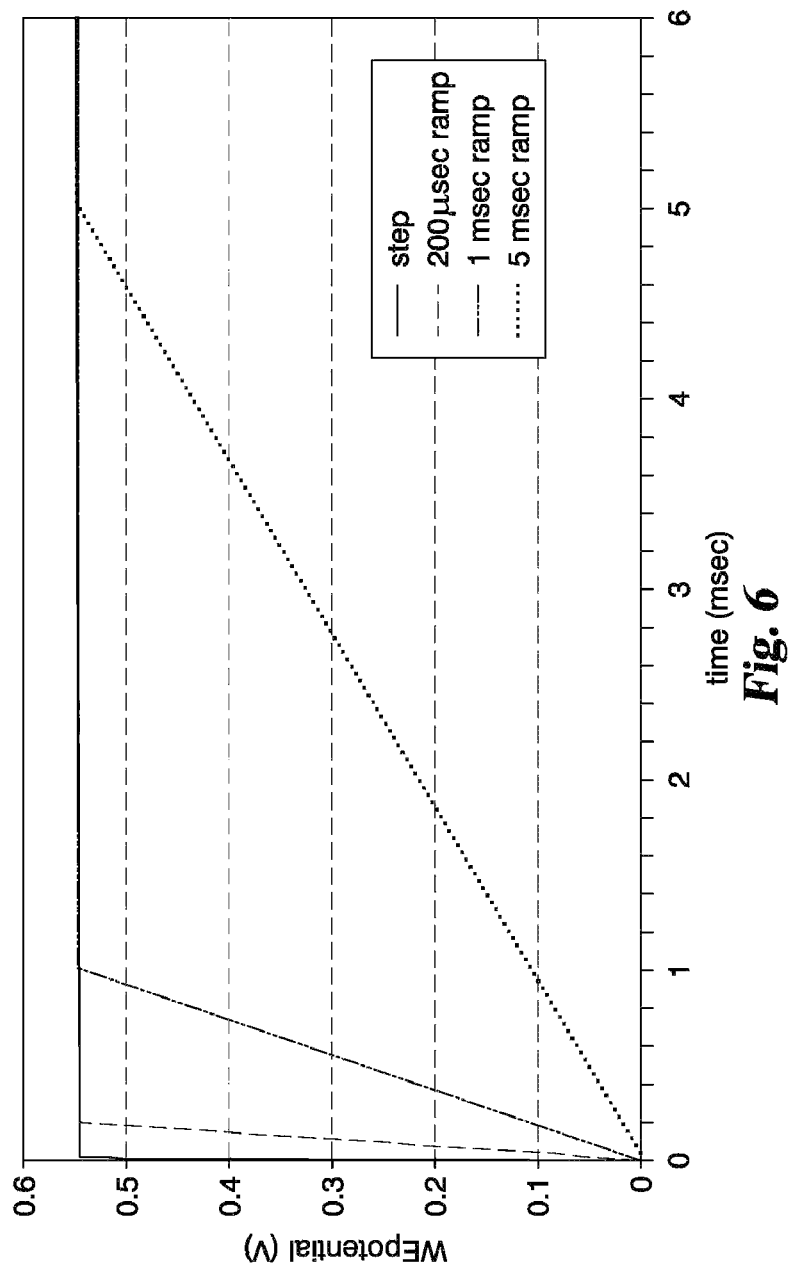
FIG. 6 is a graph that illustrates ramp-type excitation transitions with 200 μsec, 1 msec and 5 msec rise times in comparison to a step-type excitation.
Figure 7:
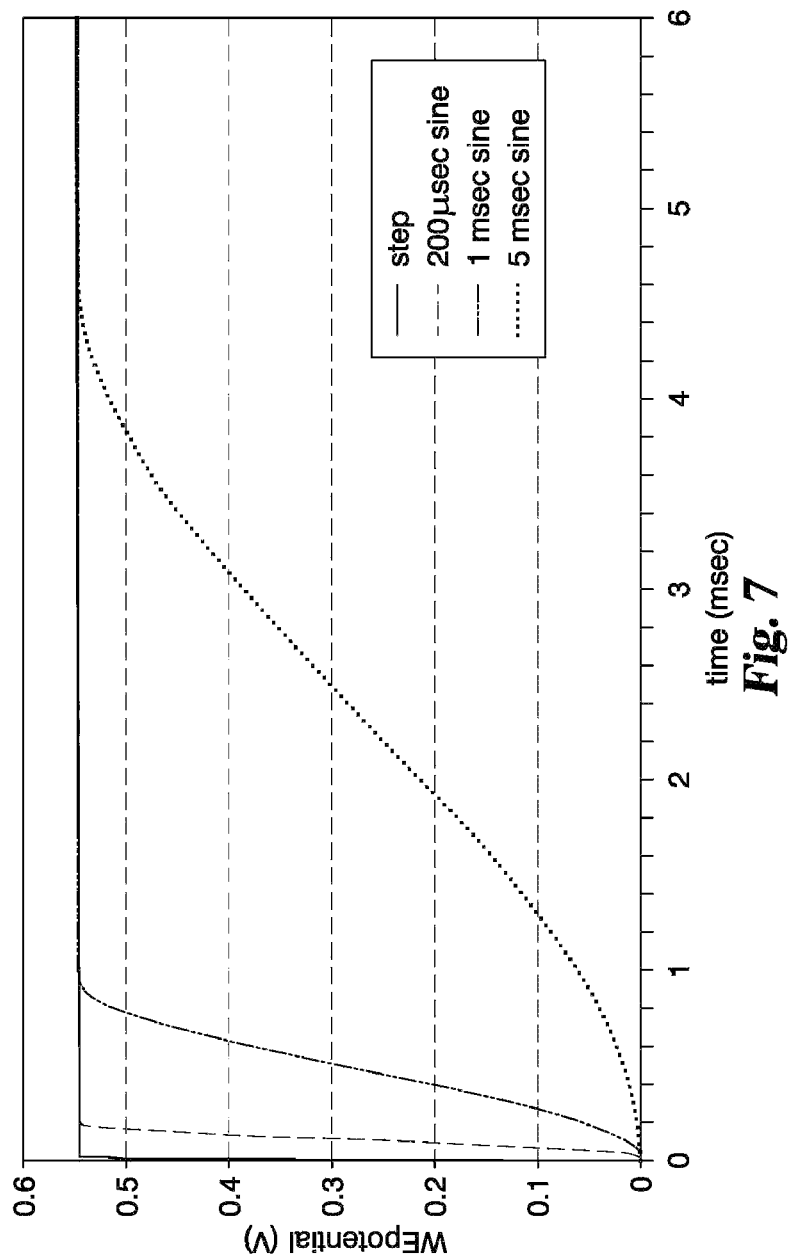
FIG. 7 is a graph illustrating half-sine wave-type excitation transitions with 200 μsec, 1 msec and 5 msec rise times in comparison to a step-type excitation.
Figure 8:
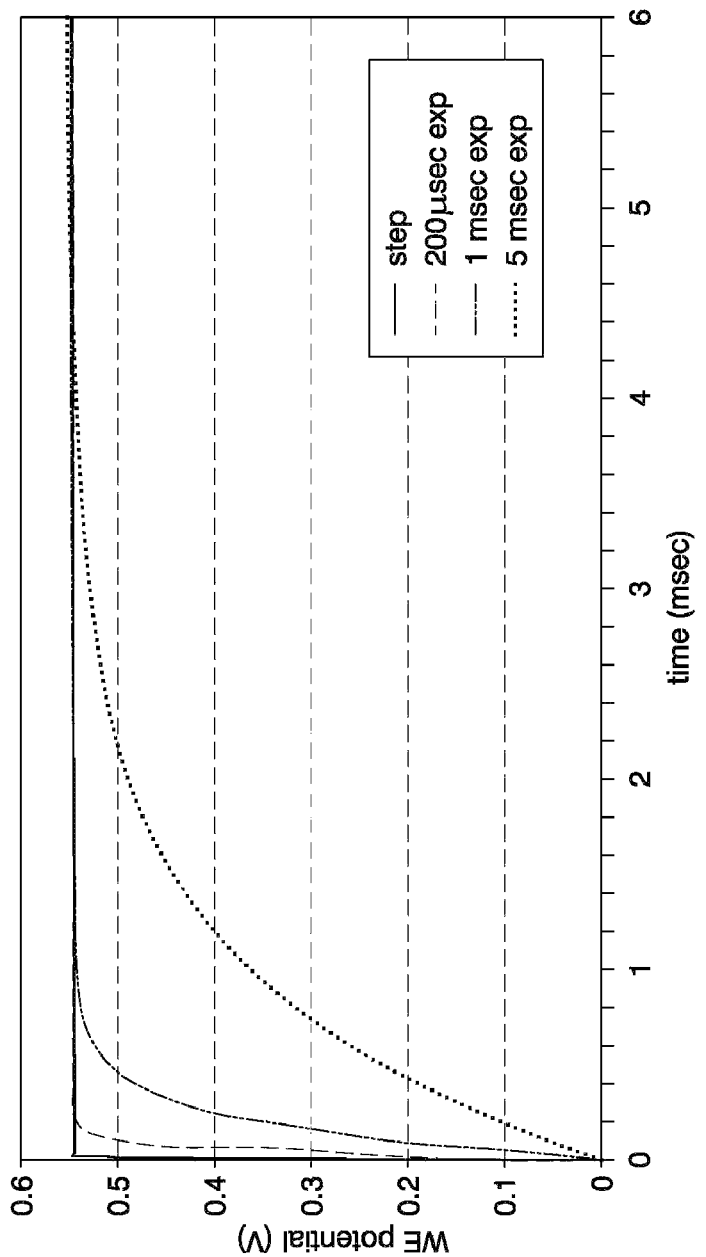
FIG. 8 is a graph illustrating exponential-type excitation transitions with 200 μsec, 1 msec and 5 msec rise times in comparison to a step-type excitation.

In the systems and methods disclosed herein, the transition of the excitation potential applied between the electrodes of the test strip is controlled so that it is at a sufficiently slow rate so as to reduce sources of excitation variability. The transition can be shaped in many forms including, but not limited to, various ramped, sinusoidal and/or exponential forms. For example, FIG. 6 shows a graph that compares a 550 mV excitation step potential to 550 mV linear ramped potentials having 200 μsec, 1 msec and 5 msec rise or transition times. Likewise, FIG. 7 shows a graph that compares a 550 mV excitation step potential to 550 mV ½ sinusoidal-shaped potential forms having 200 μsec, 1 msec and 5 msec rise times. Moreover, FIG. 8 shows a graph that compares a 550 mV excitation step potential to 550 mV exponential-shaped transition forms having 200 μsec, 1 msec and 5 msec rise times.

EXAMPLES

The invention will be more fully understood upon consideration of the following non-limiting examples, which are offered for purposes of illustration, not limitation.

Figure 9:
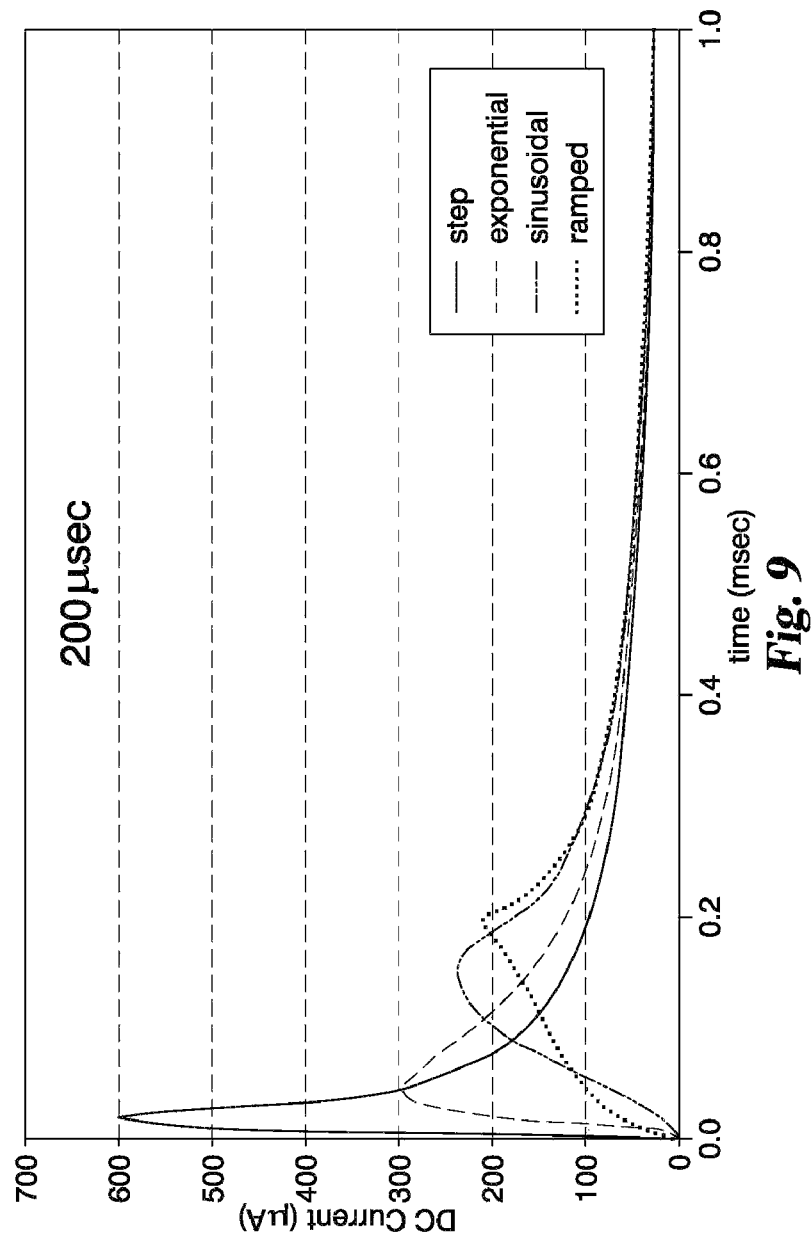
FIG. 9 is a graph illustrating the current response for step-, exponential-, sinusoidal- and ramp-type excitations with 200 μsec rise times.
Figure 10:
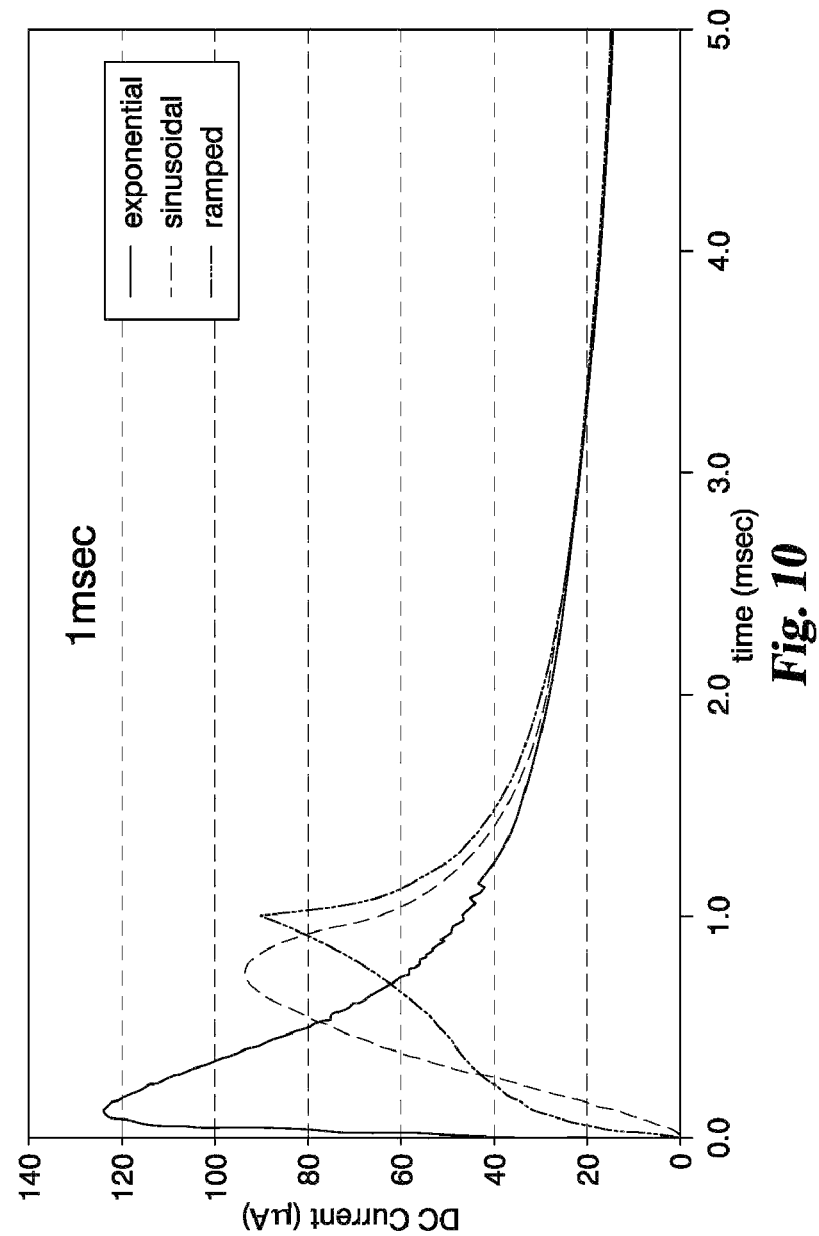
FIG. 10 is a graph illustrating the current response for exponential-, sinusoidal-, and ramp-type excitations with 1 msec rise times.
Figure 11:
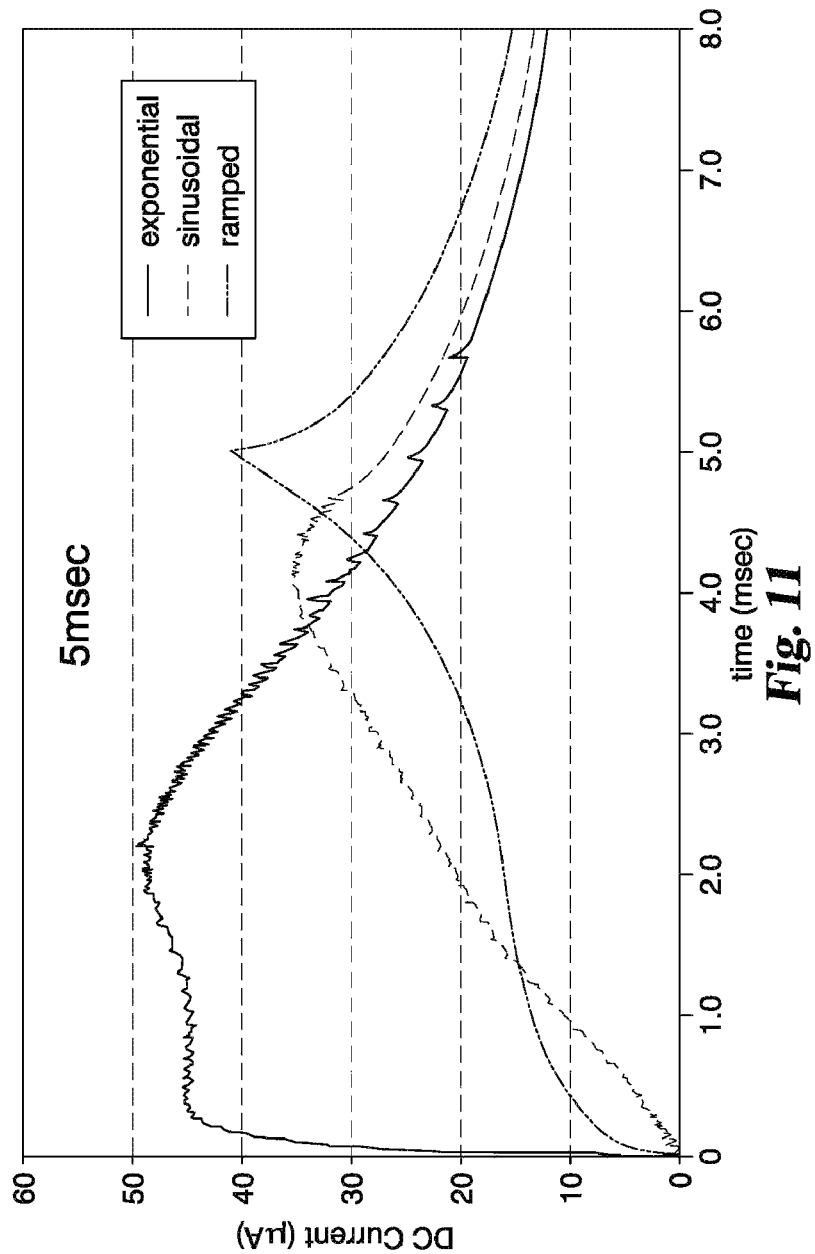
FIG. 11 is a graph illustrating the current response for exponential-, sinusoidal- and ramp-type excitations with 5 msec rise times.
Figure 12:
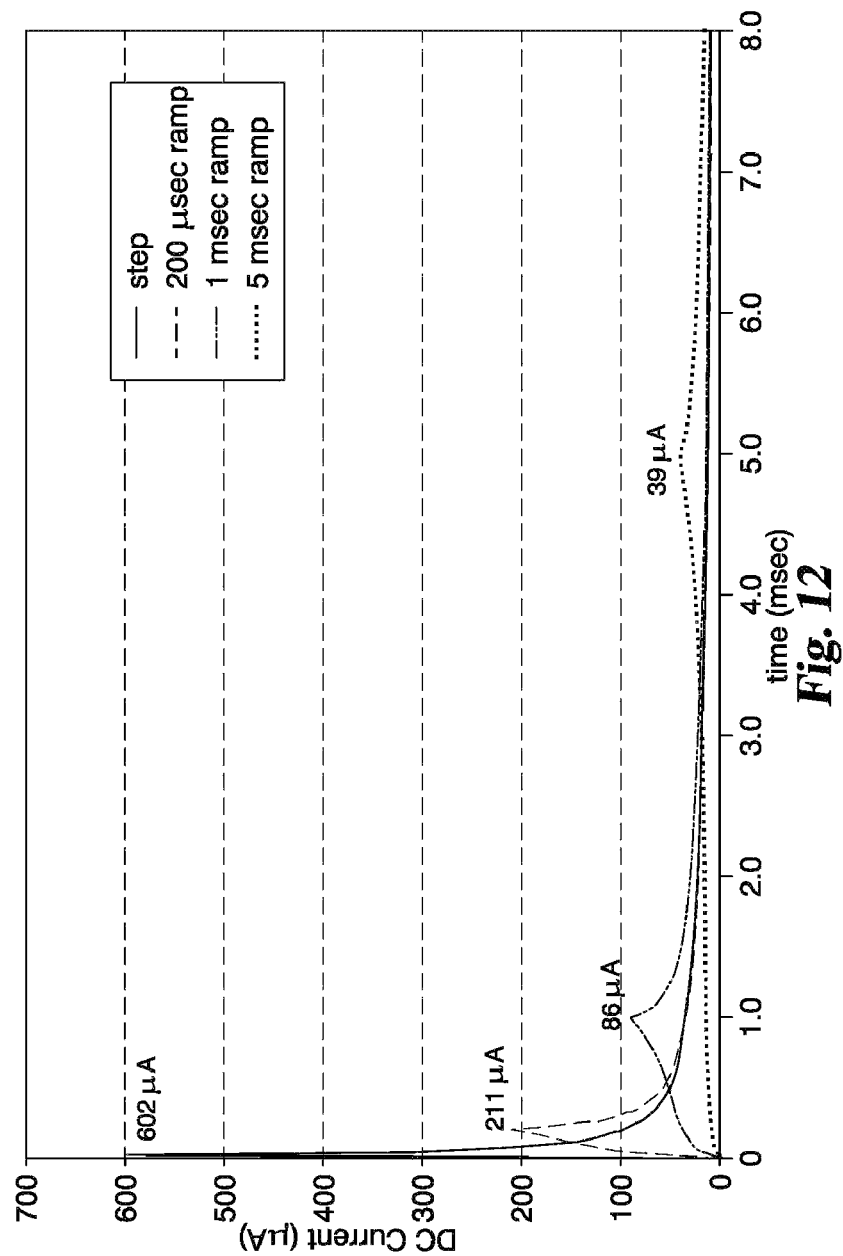
FIG. 12 is a graph illustrating the current response for ramp-type excitations with 200 μsec, 1 msec and 5 msec rise times.
Figure 13:
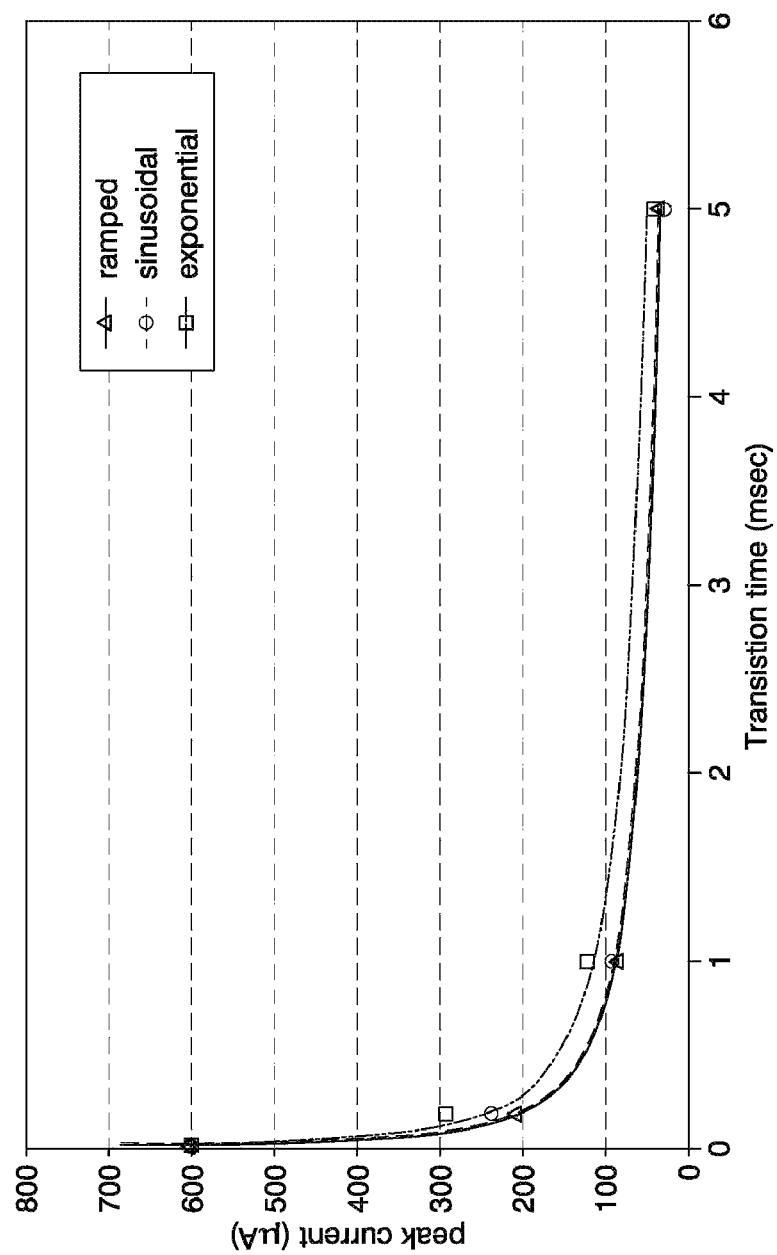
FIG. 13 is a graph of the peak current response in comparison to rise time for exponential-, sinusoidal- and ramp-type excitations.

Turning now to FIG. 9, it shows a graph of the current response to the ramped-shaped, sinusoidal-shaped and exponential-shaped 550 mV excitation potentials with the 200 μsec transition time for a glucose linearity solution with a glucose concentration of about 400 mg/dl (LIN 4). Compared to the current response of the step excitation potential also illustrated in the graph of FIG. 9, the ramped-shaped, sinusoidal-shaped, and exponential-shaped excitation potentials (i.e., the ones with the controlled transition time) have a significantly lower peak current response, with the ramped-shaped excitation potential having the smallest peak current. This reduction of the peak current response continues as the transition time becomes longer. As shown in FIGS. 10 and 11, the peak current response becomes even lower with a 1 msec transition time (FIG. 10) and still yet lower with a 5 msec transition time (FIG. 11). It should be noted that the peak current response for the step potential was not shown in FIGS. 10 and 11 because the peak current response would be off the scales in the graphs. The graph in FIG. 12 in another way shows this dramatic reduction of the peak current response as the transition time becomes longer (i.e., 200 μsec, 1 msec and 5 msec rise times) for a ramp-shaped excitation potential as compared to a step-shaped excitation potential. FIG. 13 has a graph that compares the peak current response to the transition or rise time for the ramped-, sinusoidal- and exponential-shaped excitation potentials. Again, FIG. 13 shows that for longer transition times, the peak current response is reduced. The general form for the peak current with increasing delay is approximately $K/\sqrt{(\tau)}$, regardless of waveshape. It should be noted the results illustrated in FIGS. 9-13 were conducted using an aqueous test solution with a glucose concentration of about 400 mg/dL and 30 mS/cm conductivity. Similar results in the reduction of the peak current response were obtained for different glucose concentrations.

Figure 14:
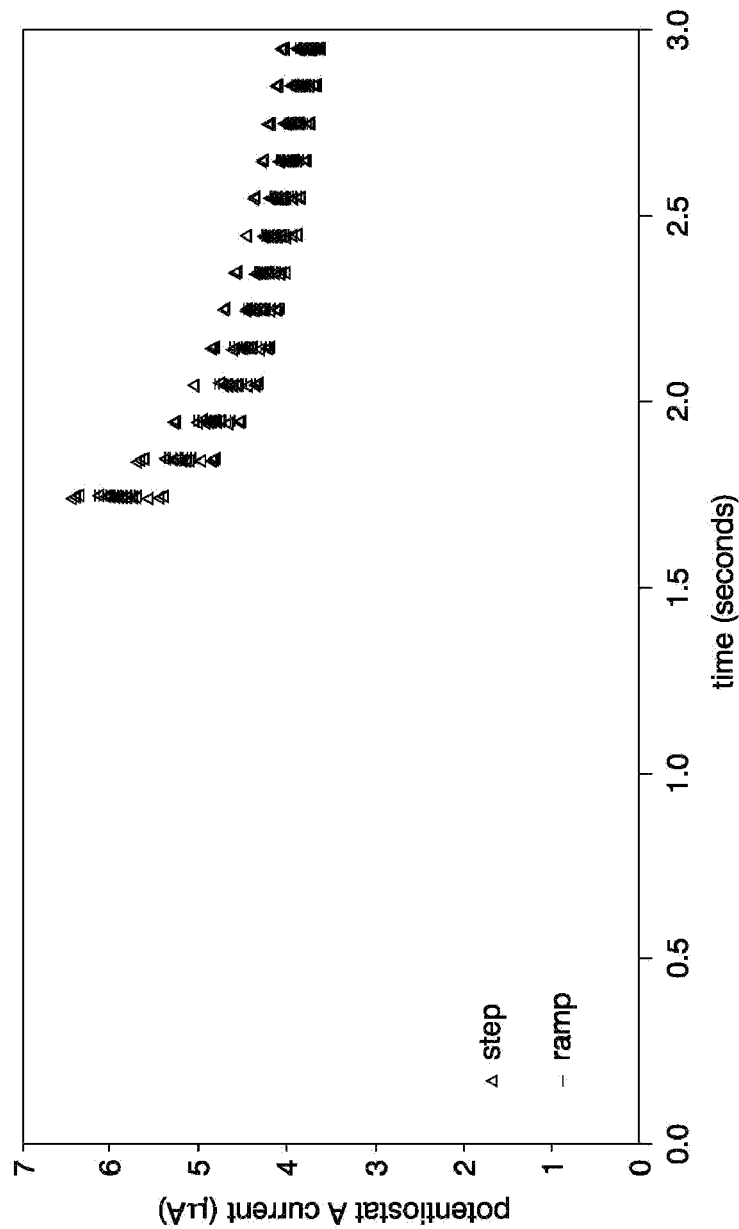
FIG. 14 is a graph of the amperometric current responses to a potential step of 450 mV and to a 10 msec ramped potential transition to 450 mV about 1.5 seconds after an about 30 mS/cm glucose test solution is applied to test strips using biosensor meter potentiostat A.
Figure 15:
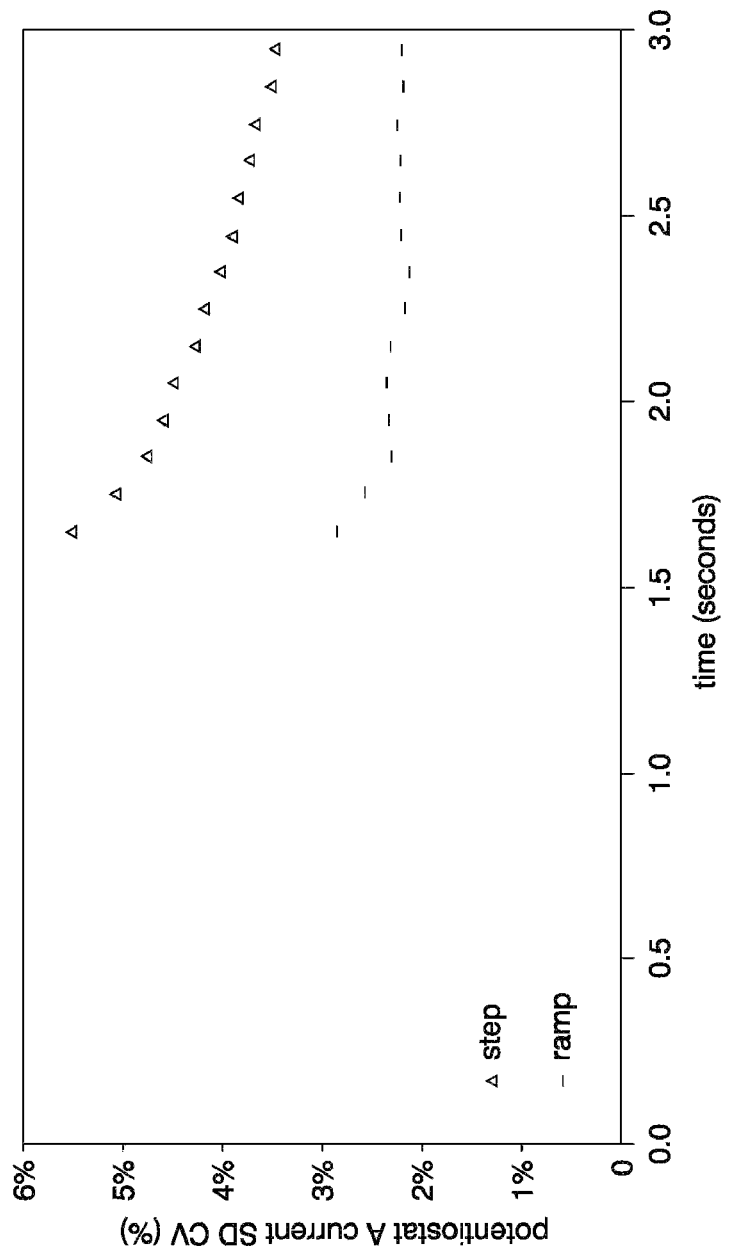
FIG. 15 is a graph of the amperometric current's standard deviation coefficient of variation (SD CV) in response to a potential step of 450 mV and to a 10 msec ramped potential transition to 450 mV about 1.5 seconds after an about 30 mS/cm glucose test solution is applied to test strips using biosensor meter potentiostat A.
Figure 16:
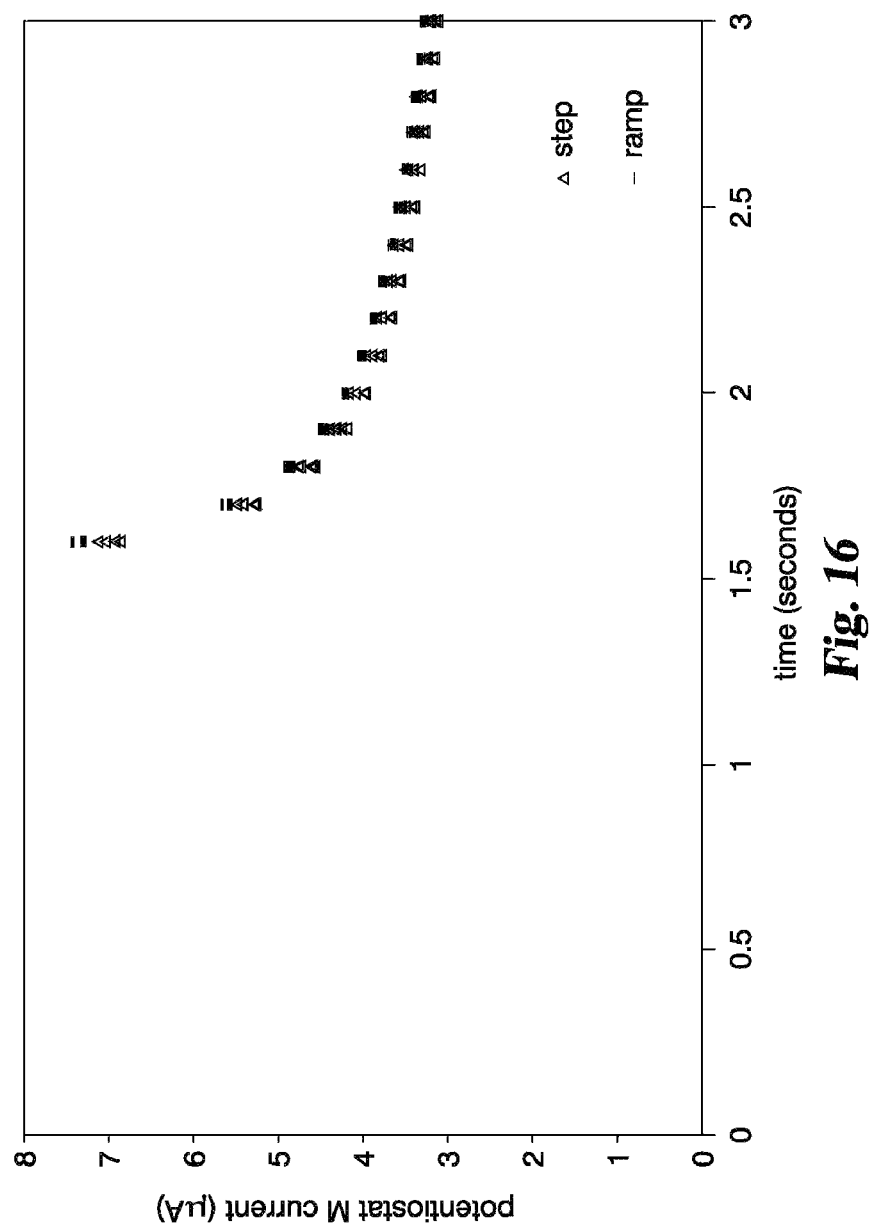
FIG. 16 is a graph of the amperometric current responses to a potential step of 450 mV and to a 10 msec ramped potential transition to 450 mV about 1.5 seconds after an about 30 mS/cm glucose test solution is applied to test strips using biosensor meter potentiostat B.
Figure 17:
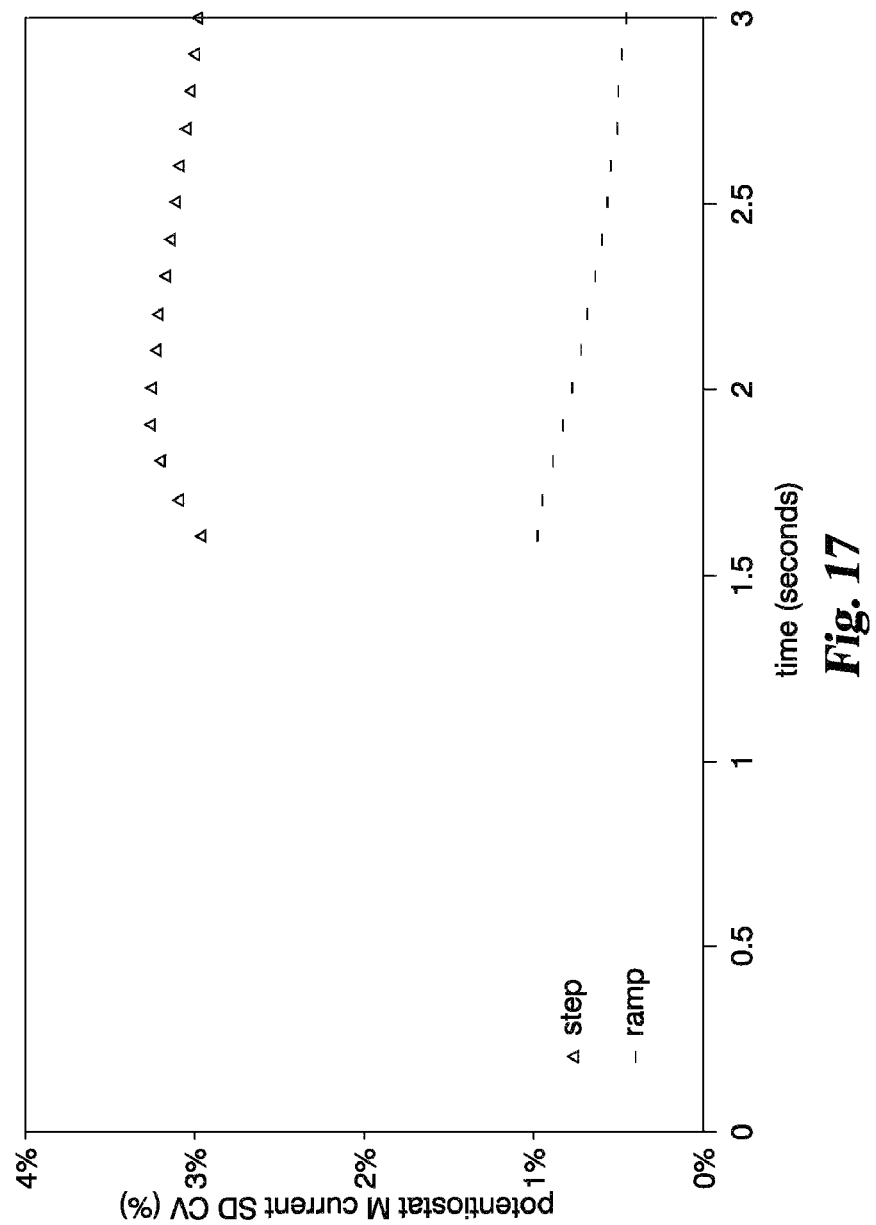
FIG. 17 is a graph of the amperometric current's SD CV in response to a potential step of 450 mV and to a 10 msec ramped potential transition to 450 mV about 1.5 seconds after an about 30 mS/cm glucose test solution is applied to test strips using biosensor meter potentiostat B.
Figure 18:
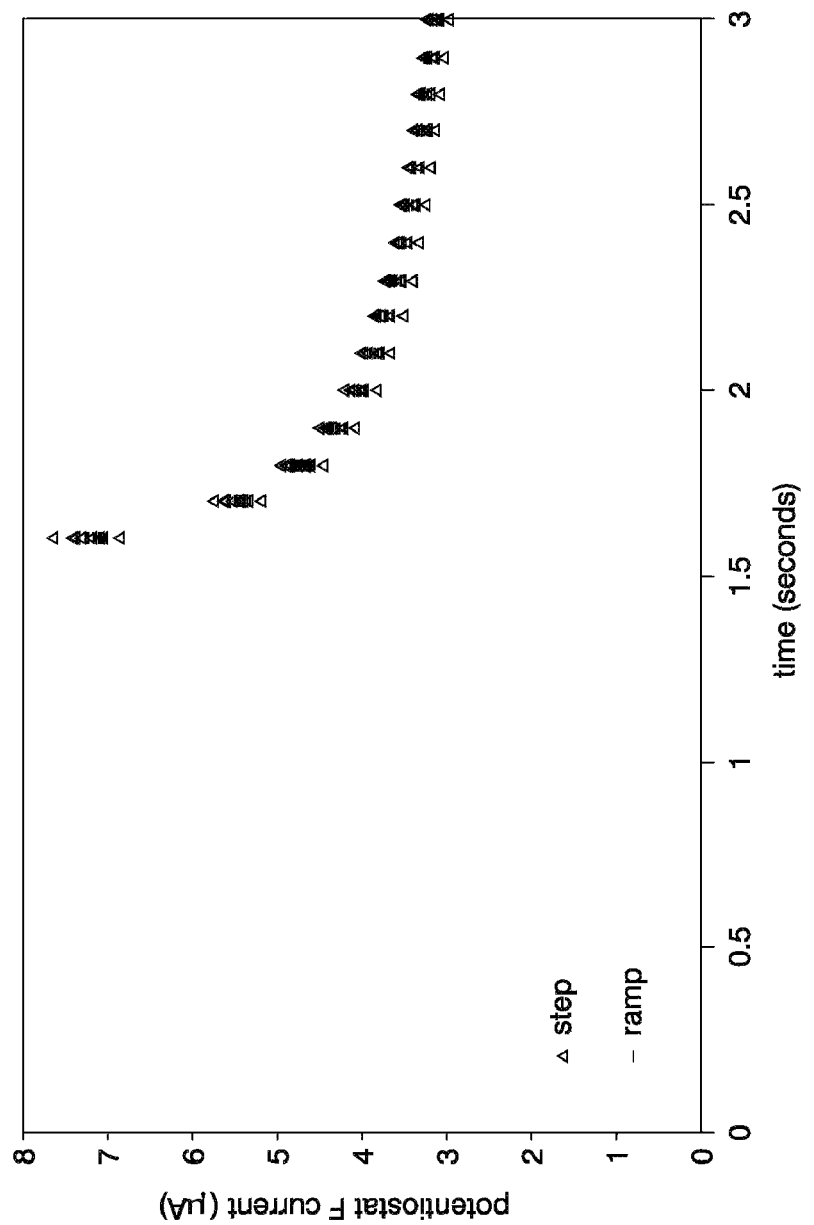
FIG. 18 is a graph of the amperometric current responses to a potential step of 450 mV and to a 10 msec ramped potential transition to 450 mV about 1.5 seconds after an about 30 mS/cm glucose test solution is applied to test strips using biosensor meter potentiostat C.
Figure 19:
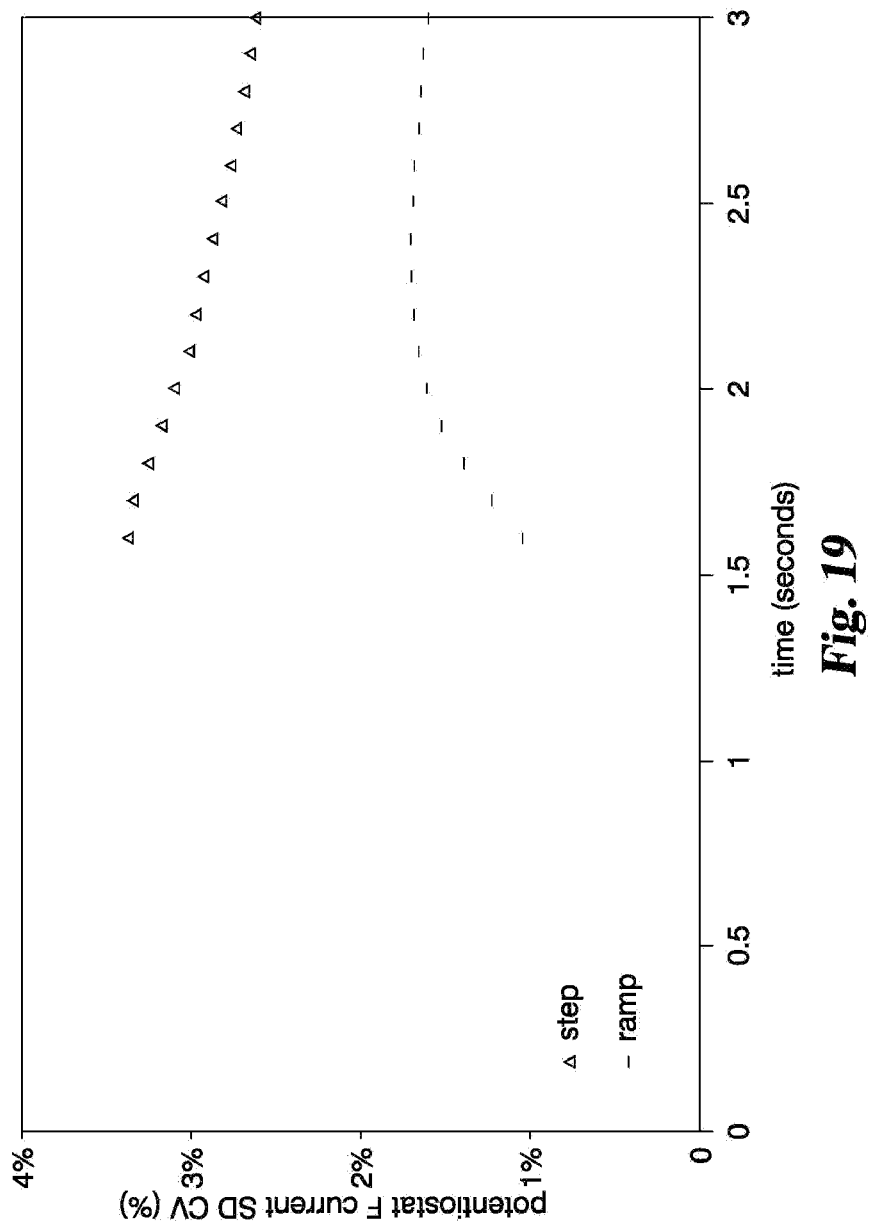
FIG. 19 is a graph of the amperometric current's SD CV in response to a potential step of 450 mV and to a 10 msec ramped potential transition to 450 mV about 1.5 seconds after an about 30 mS/cm 550 mg/dL glucose test solution is applied to test strips using biosensor meter potentiostat C.

Further experiments demonstrated the ongoing benefit of a controlled potential onset. Eight standard ACCU-CHEK AVIVA® brand test strips from lot 300749 were dosed with a 30 mS/cm linearity solution having a glucose concentration of approximately 400 mg/dl. Next, they were amperometrically measured using an ACCU-CHEK AVIVA® meter's potentiostat executing a measurement sequence that is comparable to that used with standard ACCU-CHEK AVIVA® brand test strips. The DC current response was measured for eight strips subjected to an intended 450 mV potential step after a 1.5 second incubation interval. Eight identical strips were subjected to a similar sequence, except with a 10 msec linear or ramped transition from 0 to 450 mV. In both the stepped and ramped excitation potential tests, the same aqueous test solution having a glucose concentration of approximately 400 mg/dL was used. FIGS. 14 and 15 illustrate the DC current results of this test. In FIG. 14, the test strips that were measured using the measurement sequence that is standard for ACCU-CHEK AVIVA® brand test strips established a base line upon which the stepped and ramped excitation potentials were compared. As can be seen, the sensors subjected to a stepped potential exhibited greater variability than those with a controlled transition at all times during the amperometric measurement, especially at the times closer to the excitation onset. This is most noticeable in FIG. 15, which further indicates the sensor's precision may be affected by the potentiostat transient response long after the potential is applied. The same comparison was performed using the same test strips and solutions on two other potentiostats. Similar results were obtained using both potentiostats, as shown in FIGS. 16-19. Amperometric measurement precision is improved by controlling the potential transition.

Figure 20:
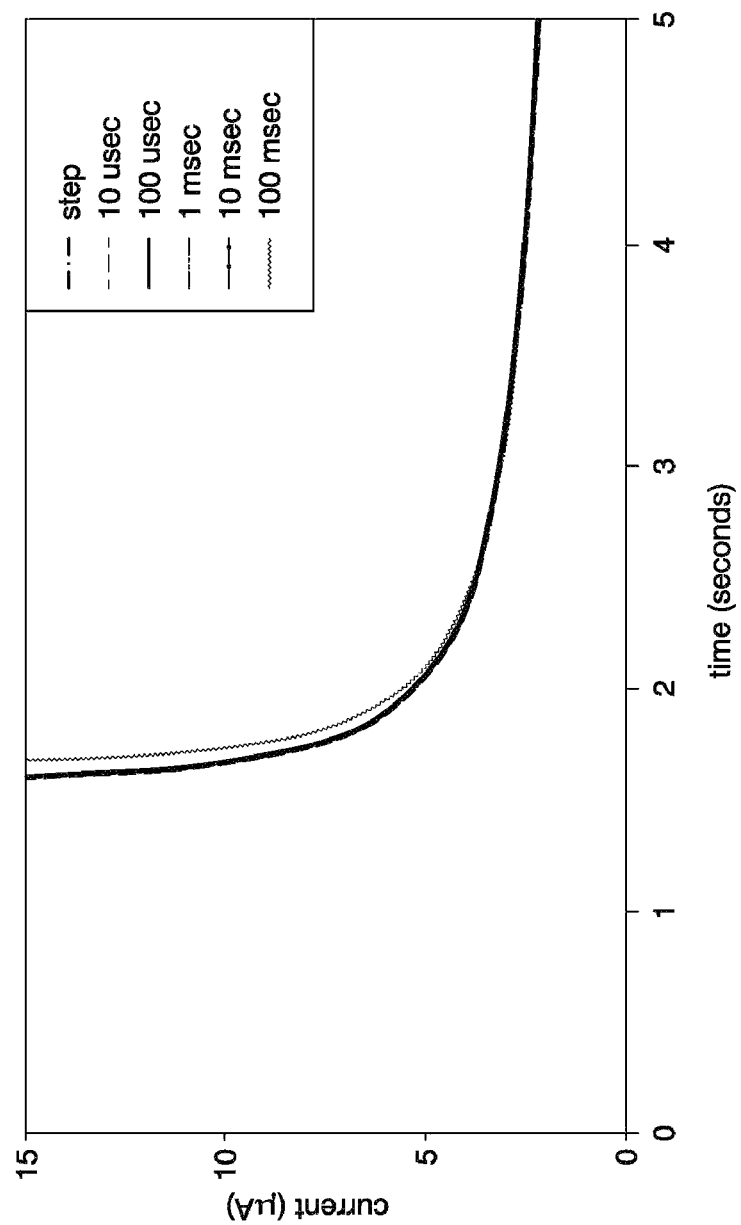
FIG. 20 is a graph of the average current response to an applied 450 mV ramp-type potential with variable rise times.
Figure 21:
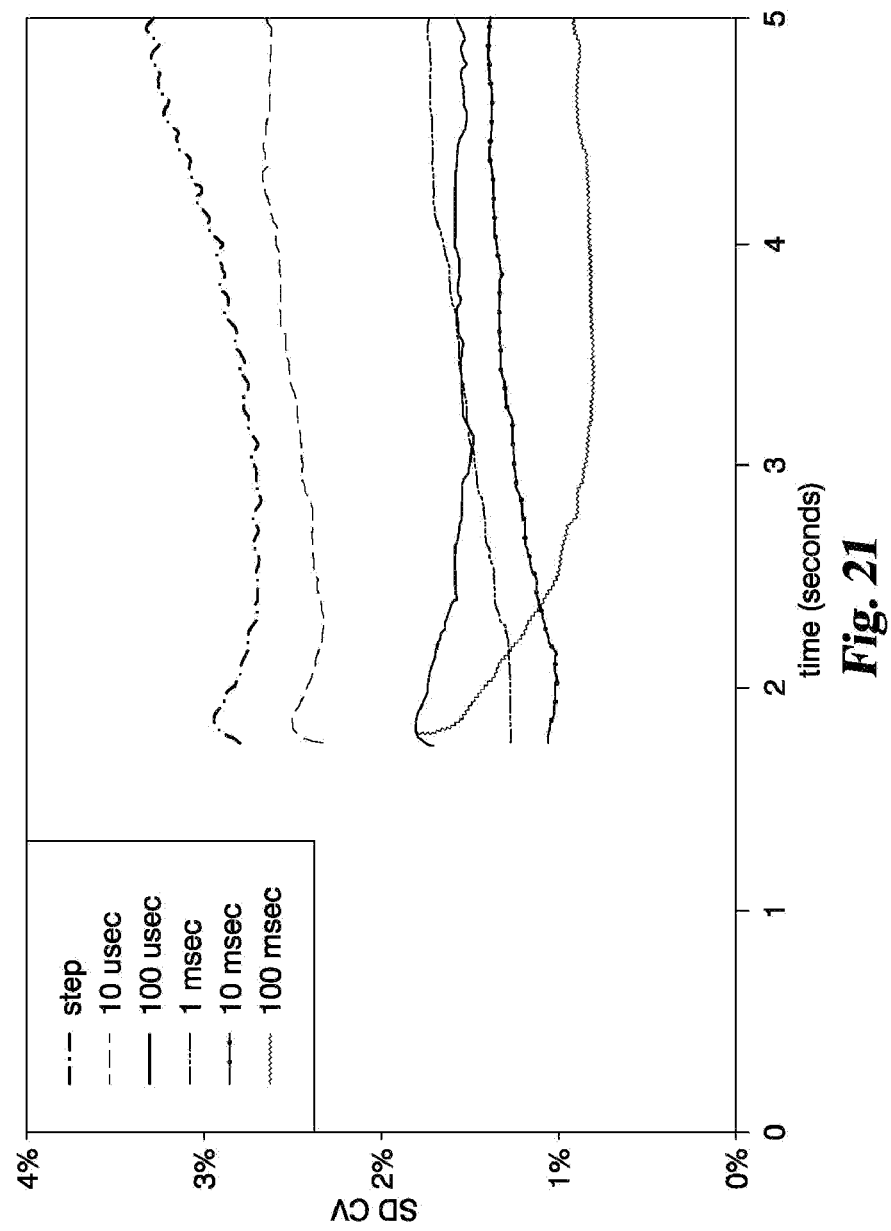
FIG. 21 is a graph of the SD CV for the current response illustrated in FIG. 20 at the variable rise times.

In still yet another experiment, uncoated ACCU-CHEK AVIVA® brand biosensor electrodes (i.e., test strips) were plasma cleaned in 250 ml/min O$_2$, 1500 ml/min Ar, 800 W for 15 minutes. The plasma-cleaned biosensors then were inserted in a high bandwidth, low slew rate potentiostat and dosed with a buffered solution of 5 mM each IrCl$_6^{2-/3-}$. The resulting current over time was measured in response to an applied 450 mV potential step with a variable rise time. In particular, the transition or rise times were 10 μsec, 100 μsec, 1 msec, 10 msec and 100 msec. The average current response, i(t), for the tested biosensors (N=8) is shown in FIG. 20. FIG. 20 demonstrates that potential rise times up to 10 msec have a small influence on the resulting i(t) current response. Potential transitions of 100 msec exhibit a more significant deviation from exhibited current response. The SD CV for the test results are shown in FIG. 21. As can be seen, the response variability generally decreases as the transition time is increased from approximately 0 seconds (i.e., at the step potential) to 100 msec. There is a substantial precision improvement for transitions of at least 100 μsec compared to a fast potential step, and limited precision advantages for transitions greater than 10 msec using this solution and biosensor.

Figure 22:
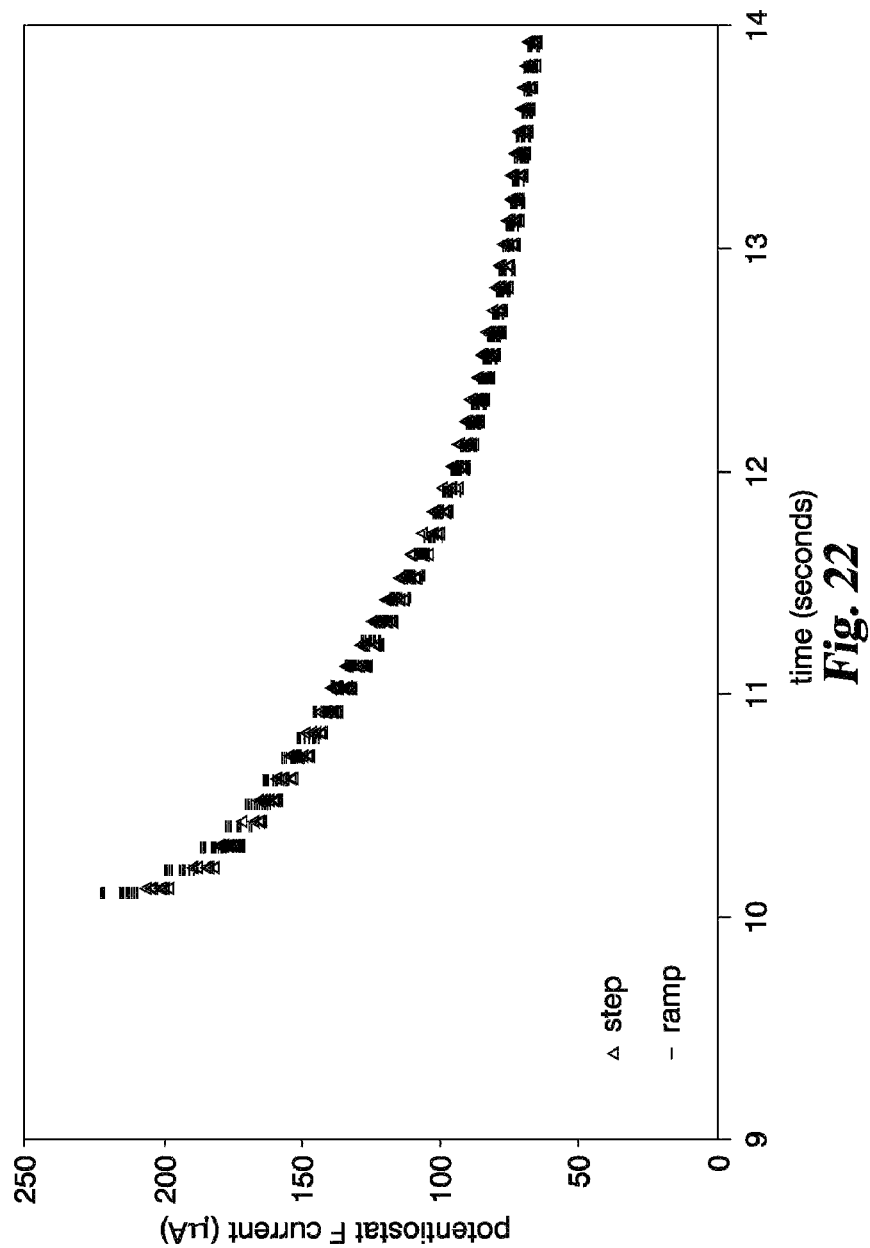
FIG. 22 is a graph of the average current response to an applied 300 mV step and a 10 msec ramped potential transition to 300 mV about 10 seconds after an about 30 mS/cm 550 mg/dL glucose test solution is applied to alternative biosensors using biosensor meter potentiostat.
Figure 23:
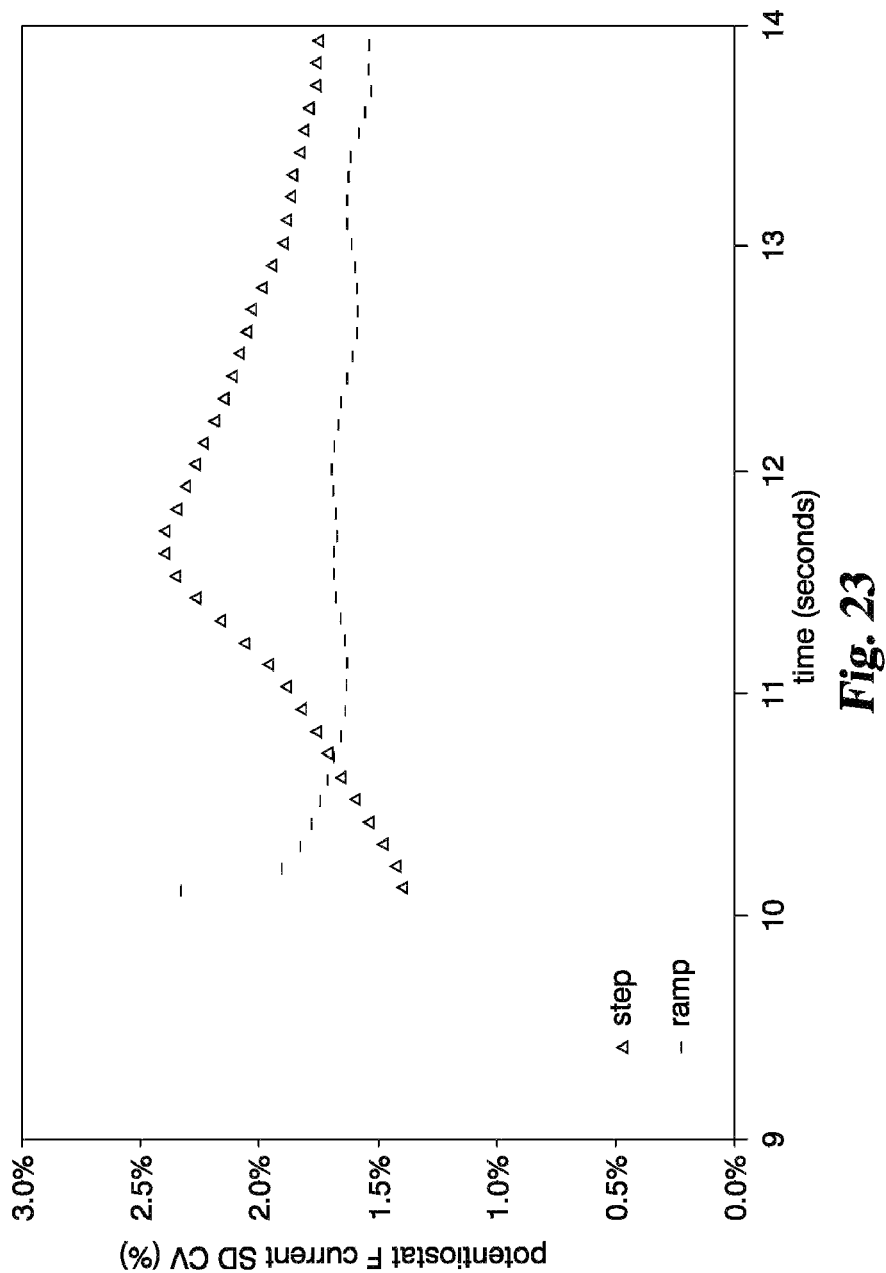
FIG. 23 is a graph of the SD CV for the current response illustrated in FIG. 22 for the two excitation transitions.

The above-described potential transitioning technique can be used at redox potentials other than at the 450 and 550 mV potentials described above. For example, FIG. 22 shows the average current response for ACCU-CHEK® COMFORT CURVE® brand test strips subjected to a 300 mV potential step and a 10 msec ramp to 300 mV after application of an about 550 mg/dL glucose test solution with 30 mS/cm conductivity. A 10 second delay occurred to approximate the test sequence used for the ACCU-CHEK® COMFORT CURVE® brand test strips. FIG. 23 is a graph of the SD CV for the response to the two excitation transitions illustrated in FIG. 22. As can be seen, amperometric measurement precision is again improved by controlling the potential transition rate.

Figure 24:
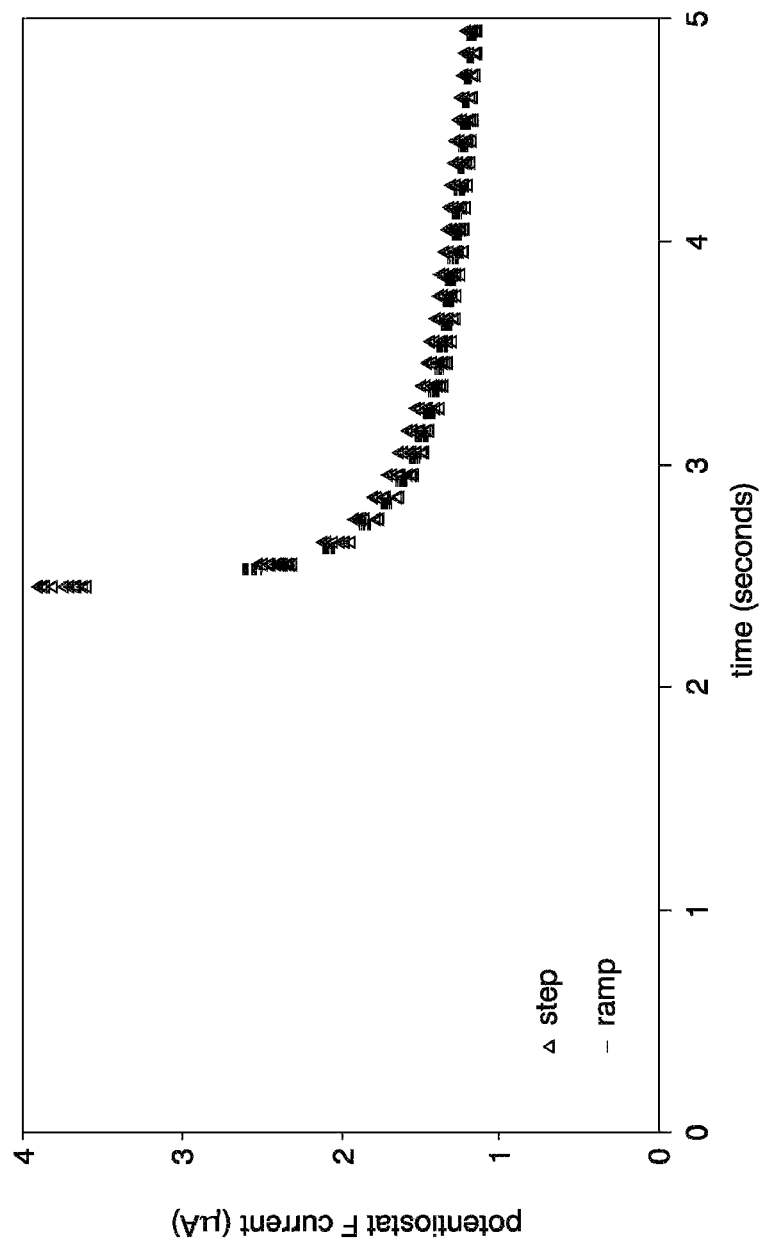
FIG. 24 is a graph of the average current response to an applied 450 mV step and a 10 msec ramped potential transition to 450 mV about 1.5 seconds after a 45 HCT, 120 mg/dL glucose whole blood sample is applied to yet other alternative biosensors using biosensor meter potentiostat F.
Figure 25:
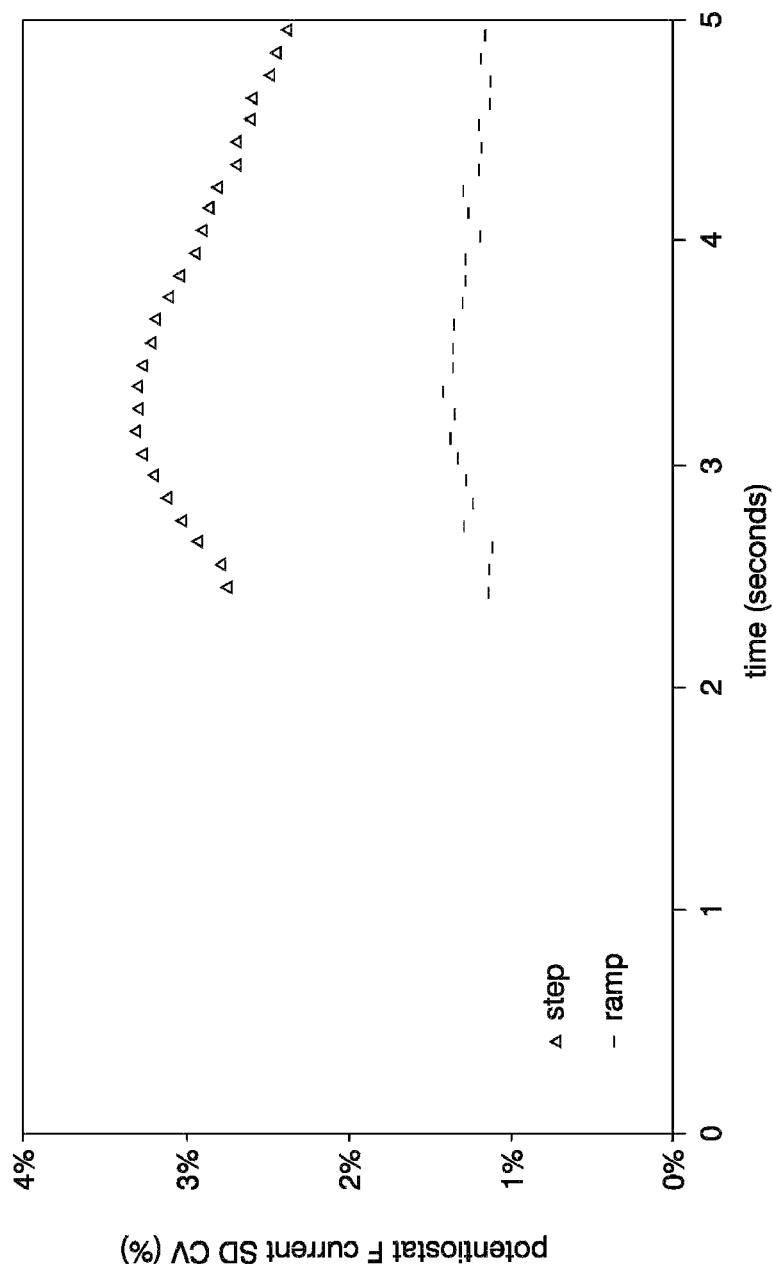
FIG. 25 is a graph of the SD CV for the current response illustrated in FIG. 22 for the two excitation transitions.

This unexpected increase in test precision created by this potential transitioning technique is not only found in aqueous test solutions but also in whole blood. FIGS. 24 and 25 demonstrate this effect for whole blood. In particular, FIGS. 24 and 25 respectively show the average current response and the SD CV for PERFORMA® test strips subjected to a 450 mV potential step and a 10 msec ramp to 450 mV after application of a 45% HCT 120 mg/dL whole blood solution. These results plainly show that controlling the potential transition at a sufficiently slow rate (i.e., below the slew rate capability of the potentiostat) improves the testing precision and reproducibility for whole blood as well.

Figure 26:
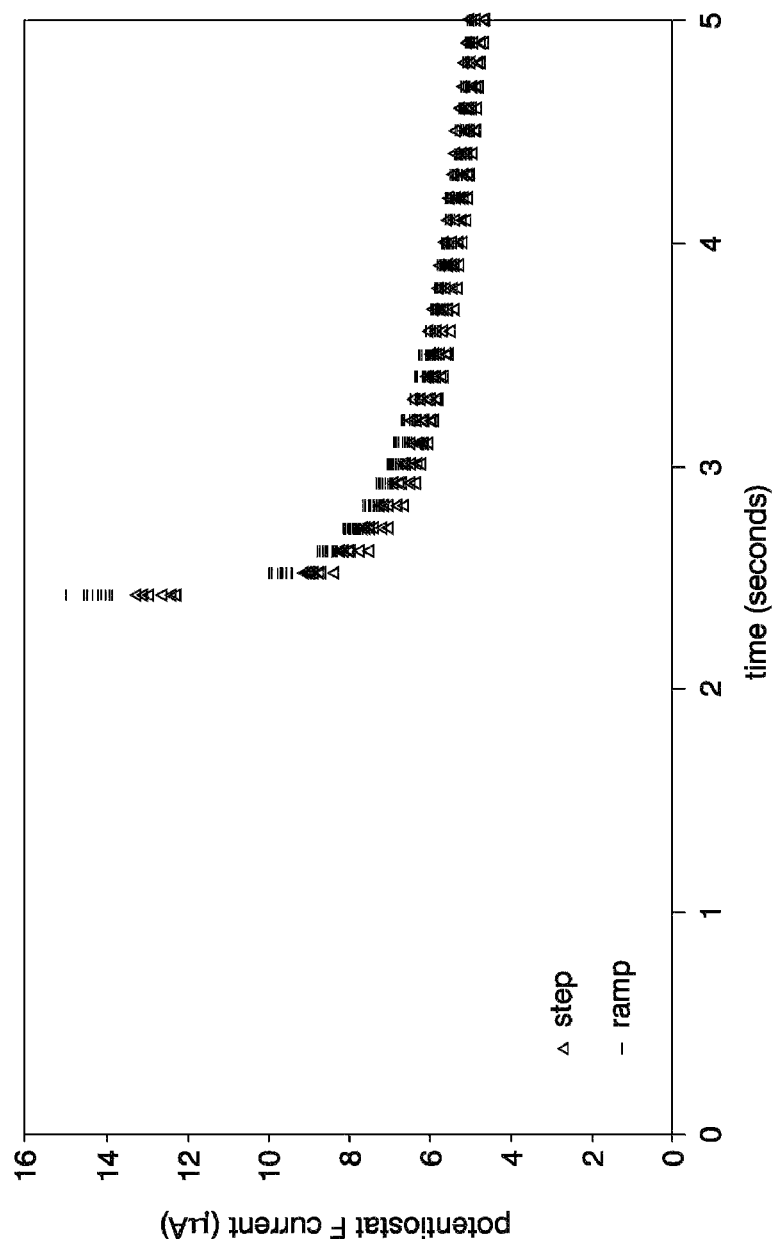
FIG. 26 is a graph of the average current response to an applied 450 mV step and a 10 msec ½ sine potential transition to 450 mV about 1.5 seconds after an about 30 mS/cm 550 mg/dL glucose test solution is applied to biosensors as used in connection with the examples from FIGS. 24 and 25, using biosensor meter potentiostat F.
Figure 27:
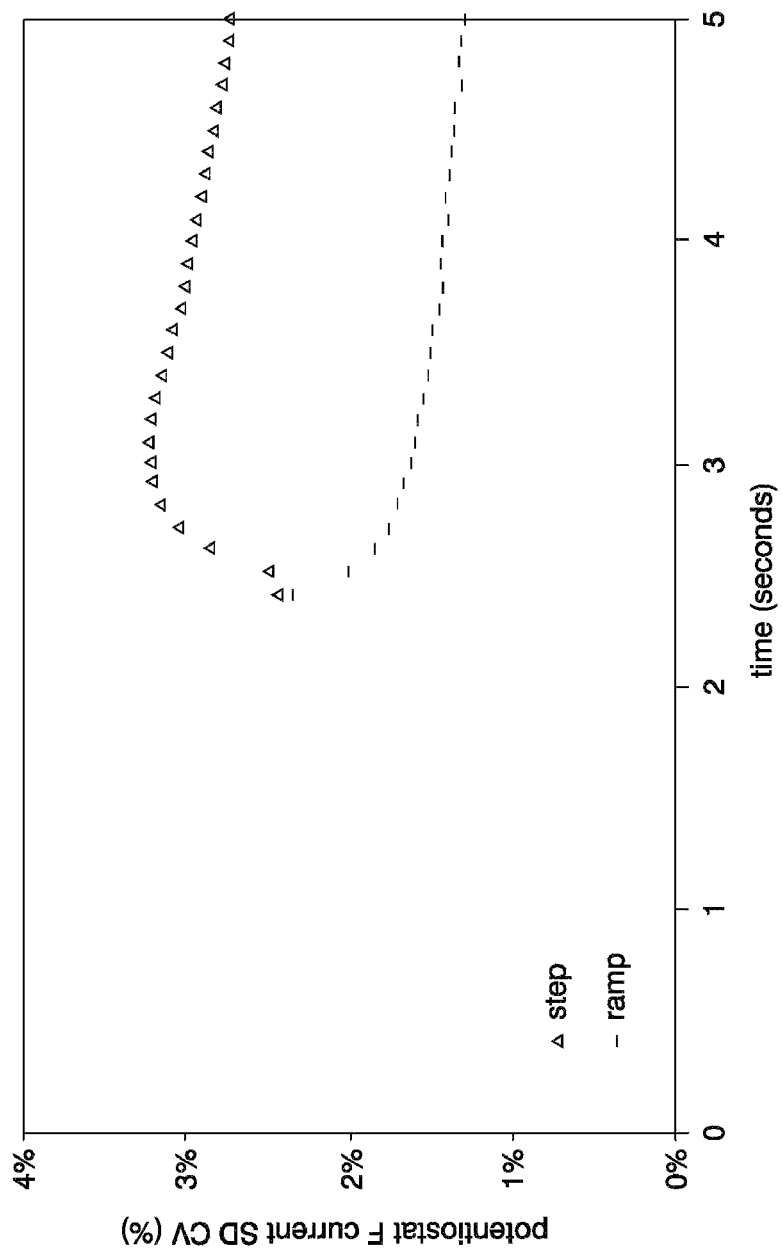
FIG. 27 is a graph of the SD CV for the current response illustrated in FIG. 22 for the two excitation transitions.

As noted above, the transition can have other shapes besides a linear-shaped ramp (see, e.g., FIGS. 7-11). For instance, FIGS. 26 and 27 respectively show the average current response and the SD CV for PERFORMA® test strips subjected to a 450 mV potential step and a 10 msec ½ sine cycle to 450 mV after application of a 550 mg/dL glucose test solution with 30 mS/cm conductivity. This sinusoidal transition is easy to generate and has a more gradual transition from 0 V and to a plateau voltage than an exponential transition.

It should be recognized from the above-discussed test results that increasing the potential transition time to at least approximately 100 μsec dramatically reduces the adverse impact due to meter/potentiostat and sample properties. This in turn facilitates more consistent readings across multiple meter platforms. Consequently, the time and expense usually devoted to implementing and refining the fundamental circuit design of the meter to match the sensor architecture when changes are made can be dramatically reduced. In other words, a particular brand or type of biosensor with specific properties can be used on two or more brands/types of meters that have different electrical characteristics with minimal differences in readings. When this technique is used, the results can be outputted in a variety of ways, such as displayed on a screen of the meter, printed on paper, and/or played on a speaker of the meter, just to name a few examples.

All of the patents, patent applications, patent application publications and other publications recited herein are hereby incorporated by reference as if set forth in their entirety.

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

The invention claimed is:

1. A method of electrochemical analysis, the method comprising the steps of:
providing an electrochemical test strip with a mediator system and electrodes;
introducing a body fluid sample to the mediator system and in contact with electrodes of the test strip;
applying an excitation potential difference between the electrodes of the test strip and across the body fluid sample, wherein the excitation potential difference has a transition time of at least 100 μsec, wherein the applying the excitation potential difference step is performed by a meter having a slew rate capability, wherein the slew rate at which the meter applies the excitation potential difference is slower than the slew rate capability of the meter, and wherein the excitation potential difference is at least 300 mV and the slew rate is at most about 900 V/sec; and
determining analyte concentration in the body fluid sample based on an electrical response to said excitation potential difference.

2. The method of claim 1, wherein the application of the excitation potential difference has a shape selected from the group consisting of a ramp-shaped waveform, a sinusoidal-shaped waveform, and an exponential-shaped waveform.

3. The method of claim 1, wherein the excitation potential difference is selected from the group consisting of at least about 300 mV, at least about 450 mV, and at least about 550 mV.

4. The method of claim 1, wherein the meter includes a processor and/or memory driven digital-to-analog converter that controls the slew rate at a rate sufficiently slow to make variations in analog electronics properties insignificant.

5. The method of claim 1, wherein the meter includes a voltage follower arrangement.

6. The method of claim 1, wherein the meter performs said applying the excitation potential difference and said determining the analyte concentration; and the method further comprising: outputting the analyte concentration with the meter.

7. The method of claim 1 further comprising the steps of:
providing a second electrochemical test strip with the mediator system and electrodes being the same type as the first electrochemical test strip;
introducing a second body fluid sample to the mediator system and in contact with electrodes of the second test strip;
applying a second excitation potential difference between the electrodes of the second test strip and across the second body fluid sample with a second meter that has different electrical properties than the meter, wherein the second excitation potential difference has a transition time of at least 5 msec; and
determining analyte concentration in the second body fluid sample based on a second electrical response to said applying the second excitation potential difference.

8. The method of claim 1, wherein the body fluid sample comprises blood and the analyte concentration includes glucose concentration.

9. The method of claim 1, wherein the determining analyte concentration step includes using an amperometric analysis technique.

10. A method of reducing measurement error between different meter platforms, the method comprising the steps of:
analyzing glucose concentrations in blood with the same type of test strips on at least two different meter platforms that have different slew rate capabilities; and performing on each of the different meter platforms an electrochemical analysis protocol in which each meter platform applies to electrodes of the test strips excitation potential differences with transition times of at least 5 msec.

11. The method of claim 10, wherein application of the excitation potential differences has a shape selected from the group consisting of a ramp-shaped waveform, a sinusoidal-shaped waveform, and an exponential-shaped waveform.

12. The method of claim 10, wherein the excitation potential differences are selected from the group consisting of at least about 300 mV, at least about 450 mV, and at least about 550 mV.

13. The method of claim 10, further comprising the step of outputting the glucose concentrations with the meter platforms.

14. A biosensor measurement system comprising:
at least a potentiostat and measurement electronics, wherein the system has a slew rate capability dependent upon one or both of the potentiostat and measurement electronics, wherein the measurement electronics comprises a processor configured to control rate of application of an excitation potential by the potentiostat of an excitation potential between two electrical terminals and having a magnitude, wherein the rate of application of the excitation potential is at a rate slower than the slew rate capability of the system and the magnitude of the excitation potential is at least 300 mV and the slew rate is at most about 900 V/sec.

15. The system of claim 14, wherein the rate of application of the excitation potential comprises a transition time between about 100 μsec and about 5 msec.

16. The system of claim 14, wherein the rate of application of the excitation potential comprises a transition time of at least about 100 μsec to reach the magnitude of the excitation potential.

17. The system of claim 14, wherein the processor is configured to control the potentiostat to apply the excitation potential in as shape selected from the group consisting of a ramp-shaped waveform, a sinusoidal-shaped waveform, and an exponential-shaped waveform.

18. The system of claim 14, wherein the magnitude of the excitation potential is at least about 450 mV or at least about 550 mV.

19. The system of claim 14, further comprising a biosensor having at least a pair of electrically isolated electrodes in electrical communication with respective ones of the two electrical terminals, wherein the biosensor further comprises an electrochemical cell defined generally by the pair of electrodes, the cell having a time constant determined at least in part by one of the resistance or capacitance of the electrodes and the resistance or capacitance of the cell having a fluid sample applied thereto, wherein the slew rate capability is at least equal to the time constant of the cell.

* * * * *